US008263337B2

(12) United States Patent
Brennan et al.

(10) Patent No.: US 8,263,337 B2
(45) Date of Patent: Sep. 11, 2012

(54) GENETIC MARKERS OF SCHIZOPHRENIA

(75) Inventors: Mark David Brennan, Jeffersonville, IN (US); D. Kay Phillips, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/282,857

(22) Filed: Oct. 27, 2011

(65) Prior Publication Data

US 2012/0040350 A1 Feb. 16, 2012

Related U.S. Application Data

(62) Division of application No. 11/859,168, filed on Sep. 21, 2007, now Pat. No. 8,067,160.

(60) Provisional application No. 60/948,392, filed on Jul. 6, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.11; 435/6.1; 435/91.1; 536/23.1; 536/24.3; 536/24.33

(58) Field of Classification Search .................. 435/6.1, 435/6.11, 91.1, 183; 436/94, 501; 536/23.1, 536/24.3, 24.33, 25.3
See application file for complete search history.

(56) References Cited

U.S. PATENT DOCUMENTS

2006/0177851 A1 8/2006 Brennan et al.
2009/0012371 A1 1/2009 Brennan et al.

OTHER PUBLICATIONS

Hennah et al., "Hapltype analysis and identification of genes for complex trait: examples from schizophrenia," *Annals of Medicine*, 36:322-331 (2004).
Riley et al., "Molecular genetics studies of schizophrenia," *European Journal of Human Genetics*, 14:669-680 (2006).
Hegele, R.A., "SNP judgment and freedom of association," *Arteriocler. Thromb. Vasc. Biol.*, 22:1058-1061 (2002).
Baker et al., "COMT Val108/158 Met modifies mismatch negativity and cognitive function in 22q11 deletion syndrome," *Biol. Psychiatry*, 58(1):23-31 (2005).
Brennan et al., "Polymorphic markers for the arylsulfatase A gene reveal a greatly expanded meiotic map for the human 22q telomeric region ," *Genomics*, 63:430-432 (2000).
Cadenhead, K.S., "Vulnerability markers in the schizophrenia spectrum: implications for phenomenology, genetics, and the identification of the schizophrenia prodrome," *Psychiatric Clinics of North America*, 25(4):837-853 (2002).
Callicott et al., "Variation in DISC1 affects hippocampal structure and function and increases risk for schizophrenia," *Proc. Natl. Acad. Sci USA*, 102(24):8627-8632 (2005).
Cannon et al., "Association of DISC1/TRAX haplotypes with schizophrenia, reduced prefrontal gray matter, and impaired short- and long-term memory," *Arch. Gen. Psychiatry*, 62(11):1205-1213 (2005).
Durand et al., "Mutations in the gene encoding the synaptic scaffolding protein SHANK3 are associated with autism spectrum disorders," *Nat. Genet.*, 39(1):25-27 (2007) [Epub Dec. 17, 2006].
Gornick et al., "Dysbindin (DTNBP1, 6p22.3) is Associated with Childhood-Onset Psychosis and Endophenotypes Measured by the Premorbid Adjustment Scale (PAS)," *J. Autism Dev. Disord.*, 35(6):831-838 (2005).
Gothelf et al., "COMT genotype predicts longitudinal cognitive decline and psychosis in 22q11.2 deletion syndrome," *Nat. Neurosci.*, 8(11):1500-1502 (2005).
Gottesman and Gould, "The endophenotype concept in psychiatry: etymology and strategic intentions," *Am. J. Psychiatry*, 160(4):636-645 (2003).
Hallmayer et al., "Genetic evidence for a distinct subtype of schizophrenia characterized by pervasive cognitive deficit," *Am. J. Hum. Genet.*, 77(3):468-476 (2005).
Harrison and Owen, "Genes for schizophrenia? Recent findings and their pathophysiological implications," *Lancet*, 361(9355):417-419 (2003).
Heinrichs, R.W., "Meta-analysis and the science of schizophrenia: variant evidence or evidence of variants?" *Neuroscience & Biobehavioral Reviews*, 28(4):379-394 (2004).
Kaufmann et al., "NIMH Genetics Initiative Millenium Schizophrenia Consortium: linkage analysis of African-American pedigrees," *Am. J. Med. Genet.*, 81:282-289 (1998).
Kavenoff et al., "One the nature of chromosome-sized DNA molecules," *Cold Spring Harbor Symposia on Quantitative Biology*, 38:1-8 (1974).
Kendler et al., "Evaluating the spectrum concept of schizophrenia in the Roscommon Family Study," *Am. J. Psychiatry*, 152(5):749-754 (1995).
Mattila et al., "Fidelity of DNA synthesis by the *Thermococcus litoralis* DNA polymerase—an extremely heat stable enzyme with proofreading activity," *Nucleic Acids Res.*, 19:4967-4973 (1991).
Saiki et al., "Analysis of enzymatically amplified beta-globin and HLA-DQ alpha DNA with allele-specific oligonucleotide probes," *Nature*, 324:163-166 (1986).
Sheffield et al., "Attachment of a 40-base-pair G + C-rich sequence (GC-clamp) to genomic DNA fragments by the polymerase chain reaction results in improved detection of single-base changes," *Proc. Natl. Acad. Sci. USA*, 86:232-236 (1989).
Pearson et al., "How to Interpret a Gemone-wide Associate Study," *JAMA*, 299:1335-1344 (2008).
Stefansson et al., "Common variants conferring risk of schizophrenia," *Nature*, 460:744-747 (2009).
Shi et al., "Common variants on chromosome 6p22.1 are associated with schizophrenia," *Nature*, 460:753-757 (2009).
International Search Report for PCT/US07/78399, mailed Oct. 1, 2008, completed Aug. 27, 2008.
Written Opinion of International Searching Authority for PCT/US07/78399, completed Aug. 27, 2008.
International Preliminary Report on Patentability for PCT/US07/78399 issued Jan. 12, 2010.

*Primary Examiner* — Frank W Lu
(74) *Attorney, Agent, or Firm* — Fish & Richardson P.C.

(57) ABSTRACT

The invention includes method of determining if a subject has a genetic predisposition to clinically diagnosed schizophrenia (SZ), schizotypal personality disorder (SPD), and/or schizoaffective disorder (SD).

18 Claims, 1 Drawing Sheet

GENETIC MARKERS OF SCHIZOPHRENIA

CLAIM OF PRIORITY

This application is a divisional application of U.S. patent application Ser. No. 11/859,168, filed on Sep. 21, 2007, now U.S. Pat. No. 8,067,160B2 which claims the benefit of U.S. Provisional Patent Application Ser. No. 60/948,392, filed on Jul. 6, 2007. The entire contents of each of these applications are hereby incorporated by reference.

FEDERALLY SPONSORED RESEARCH OR DEVELOPMENT

This invention was made with Government support under Grant No. R01 HD29888 awarded by the National Institutes of Health. The Government has certain rights in the invention.

STATE SPONSORED RESEARCH OR DEVELOPMENT

This invention was made in part with Grant No. CIF-127-COM from the Kentucky Science and Technology Corporation under Contract No. 144-401-06 to the University of Louisville and by Kentucky Science and Technology Corporation Research and Development Voucher Contract #145-402-26 to SureGene, LLC.

TECHNICAL FIELD

This invention relates to genetic markers of schizophrenia (SZ), schizotypal personality disorder (SPD), and/or schizoaffective disorder (SD), and methods of use thereof.

BACKGROUND

Normal variation for the personality trait of schizotypy may have origins that overlap the etiological factors that produce the psychiatric disease schizophrenia. Although schizophrenia has been widely researched in many disciplines for decades, the causes of this complex disease still remain elusive. For diseases where factors influencing ordinary variation in the population are the same as those that are etiologically relevant to the diagnosis of disease, a large unselected sample may contribute beneficially to research on many traits instead of just one. Furthermore, the use of quantitative measures in such a sample provides the advantage of tapping into variation in the low and middle ranges, not just the diagnostically significant high ends of trait distributions.

SUMMARY

A whole autosomal screen was conducted for quantitative trait loci (QTLs) influencing adult schizotypy as measured by the schizophrenia scale of the MINNESOTA MULTIPHASIC PERSONALITY INVENTORY-2 (MMPI-2) test (Hathaway and McKinley, 1989, supra). Tests for linkage based on a nonclinical sample of 1,065 sibling and dizygotic (DZ) twin pairs revealed a significant linkage on chromosome 4p15.1 spanning D2S391 and a highly suggestive linkage on 22q13.33 between D22S526 and D22S1744. These results point to two chromosomal regions that are associated with the etiology of schizophrenia and other psychiatric disorders.

TABLE A

SNP Markers Used for TDT Analysis (NCBI Genome Build 36.2)

| Gene Name | Chromosome | Marker | Position Mb | Alleles |
|---|---|---|---|---|
| PI4K2B | 4p15.2 | rs313548 | 24.8465 | C/T |
| PI4K2B | 4p15.2 | rs313567 | 24.8631 | C/T |
| KCNIP4 | 4p15.31 | rs6447982 | 20.3693 | A/C |
| KCNIP4 | 4p15.31 | rs10016449 | 20.4178 | C/T |
| KCNIP4 | 4p15.31 | rs3765119 | 20.4611 | C/T |
| KCNIP4 | 4p15.31 | rs1364836 | 20.9425 | C/T |
| CERK | 22q13.31 | rs801720 | 45.4608 | G/T |
| CERK | 22q13.31 | rs135667 | 45.4624 | C/G |
| CERK | 22q13.31 | rs135678 | 45.4725 | C/T |
| CERK | 22q13.31 | rs135693 | 45.4812 | C/G |
| CERK | 22q13.31 | rs1548977 | 45.5093 | A/G |
| CERK | 22q13.31 | rs710123 | 45.5239 | A/G |
| SHANK3 | 22q13.3 | rs713692 | 49.4566 | C/T |
| SHANK3 | 22q13.3 | rs9616915 | 49.4644 | C/T |
| SHANK3 | 22q13.3 | rs9616816 | 49.4704 | A/G |
| SHANK3 | 22q13.3 | rs739365 | 49.4872 | C/T |
| SHANK3 | 22q13.3 | rs6010063 | 49.5038 | A/G |
| SHANK3 | 22q13.3 | rs756638 | 49.5186 | A/G |

Single nucleotide polymorphism (SNP) markers in a number of genes (including SH3 and Multiple Ankyrin Repeat Domains 3 (SHANK3), Kv Channel Interacting Protein 4 Gene (KCNIP4), Ceramide Kinase Gene (CERK), and Phosphatidylinositol 4-Kinase Type 2 Beta Gene (PI4K2B)) were used to evaluate families from the NIMH Schizophrenia Genetics Initiative. Based on the results, an association of each of these genes with schizophrenia spectrum disorders was identified. Thus, the invention includes methods of determining risk of developing schizophrenia (SZ), schizotypal personality disorder (SPD) or schizoaffective disorder (SD) as described herein.

In one aspect, the invention includes methods for obtaining information regarding a subject's risk for developing SZ, SD or SPD. The methods include obtaining a test haplotype associated with schizophrenia as described herein. The methods can also include obtaining a sample comprising genomic DNA (gDNA) from the subject, and determining the identity, absence or presence of a test haplotype associated with SZ, SD or SPD as described herein. In some embodiments, the methods include obtaining a test haplotype for the subject comprising at least one test marker that is listed in Table A, or is within 1 linkage disequilibrium unit (1 LDU) of a marker listed in Table A, wherein the haplotype provides information regarding the subject's risk of developing SZ, SPD, or SD. In some embodiments, the test marker is a marker listed in one or more of Table A, or a marker within 1 linkage disequilibrium unit (1 LDU) or a D'>0.75 of a polymorphism described herein, e.g., markers in a region of chromosome 4p or 22q, e.g., in 22q13, e.g., in 4p between and including SNPs rs313548 and rs313567 at the PI4K2B locus and/or between rs6447982 and rs1364836 at the KCNIP4 locus; and/or in 22q13, e.g., between rs801720 and rs710123 at the CERK locus, and/or between rs713692 and rs756638 at the SHANK3 locus.

In some embodiments, the test haplotype includes at least one marker listed in Table A, e.g., two or more markers listed in Table A. In some embodiments, the test haplotype includes two or more markers from one gene, or from each gene if two or more genes are used. In some embodiments, the test haplotype includes at least two markers, each from a different gene listed in Table A.

In some embodiments, the test haplotype includes at least one marker listed in Table A and provides information regarding a subject's risk of developing SZ, under a narrower (DSM III/DSMIV) disease definition.

In some embodiments, the test haplotype provides information regarding a subject's risk of having a particular endophenotype, and/or one or more specific symptoms, e.g., hallucinations, paranoia, mania, depression, obsessive-compulsive symptoms, etc., as well as response or lack of response to drugs and comorbidity for substance and alcohol abuse.

The methods described herein can include obtaining a haplotype that includes two or more, e.g., two, three, four, five, or six markers.

Additionally, the methods can include determining the presence or absence of other markers known to be associated with SZ, SD or SPD, e.g., outside of a region identified herein. A number of other such markers are known in the art, e.g., as described herein.

The subject can be a mammal, e.g., a primate, preferably a higher primate, e.g., a human (e.g., a patient having, or at risk of, SZ, SD or SPD). In one embodiment, the subject is a patient having SZ, SD or SPD (e.g., a patient suffering from early, intermediate or aggressive SZ, SD or SPD). In some embodiments, the methods described herein are used to obtain information regarding a subject's risk of developing SZ, SD or SPD, wherein the disorder is other than catatonic schizophrenia. In some embodiments, the subject is of African American (AA) or European American (EA) descent, i.e., has one or more ancestors who are AA or EA.

In one embodiment, a subject to be evaluated by a method described herein is a subject having one or more risk factors associated with SZ, SPD or SD. For example, the subject may have a relative afflicted with SZ, e.g., one or more of a grandparent, parent, uncle or aunt, sibling, or child who has or had SZ, SPD or SD; the subject may have a genetically based phenotypic trait associated with risk for SZ, SPD or SD (e.g., eye tracking dysfunction); deficits in working (short-term) memory; and/or mixed-handedness (the use of different hands for different tasks), particularly in females.

In some embodiments, the subject is a child, fetus, or embryo, and one of the subject's relatives, e.g., a parent or sibling, of the child, fetus, or embryo has SZ, SPD or SD. In this case, the presence in the child, fetus, or embryo of a haplotype described herein that is shared with the affected parent, but not with the non-affected parent, indicates that the child, fetus, or embryo has an increased risk of developing SPD, SD, or SZ. In some embodiments, the subject has no overt or clinical signs of SZ, SPD, or SD.

In some embodiments, obtaining a test haplotype includes obtaining a sample comprising DNA from the subject; and determining the identity, presence or absence of at least one test marker that is listed in Table A, or is within 1 LDU (in the particular population) of a marker listed in Table A, in the DNA. The sample can be obtained, e.g., from the subject by a health care provider, or provided by the subject without the assistance of a health care provider.

In some embodiments, obtaining a test haplotype includes reviewing a subject's medical history, wherein the medical history includes information regarding the presence or absence of at least one test marker that is listed in Table A, or is within 1 LDU of a marker listed in Table A, in the subject.

In some embodiments, the methods described herein include obtaining a reference haplotype including a reference marker that corresponds to a test marker, and comparing the test haplotype to the reference haplotype. A reference marker that "corresponds to" a test marker is the same marker. For example, if the test haplotype includes rs313548, then the reference haplotype should also include rs313548 for comparison purposes; or if the test haplotype includes rs10016449, then the reference haplotype should also include rs10016449 for comparison purposes; or if the test haplotype includes rs1548977, then the reference haplotype should also include rs1548977 for comparison purposes; or if the test haplotype includes rs9616816, then the reference haplotype should also include rs9616816 for comparison purposes.

The sharing of a haplotype (e.g., of some or all of the markers) between the test haplotype and a reference haplotype is indicative of whether there is an increased likelihood that the subject will develop SZ, SPD, or SD.

In some embodiments, the methods include administering a treatment to a subject identified as being at increased risk for developing SZ, SPD, or SD, e.g., a pharmacological or psychosocial treatment as described herein. In some embodiments, the subject has no overt or clinical signs of SZ, SPD, or SD, and the treatment is administrated before any such signs appear.

Information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in a clinical trial, e.g., a trial of a treatment for SZ, SPD, or SD. The methods include obtaining a haplotype for the subject including at least one marker that is listed in Table A, or is within 1 linkage disequilibrium unit (1 LDU) of a marker listed in Table A; determining whether the haplotype is associated with an increased risk of developing schizophrenia (SZ), schizotypal personality disorder (SPD), or schizoaffective disorder (SD); and including the subject in the trial if the haplotype indicates that the subject has an increased risk of developing SZ, SPD, or SD.

In another aspect, the invention provides methods for selecting a subject for administration of a treatment for schizophrenia (SZ), schizotypal personality disorder (SPD), or schizoaffective disorder (SD). The methods include obtaining a haplotype for the subject, wherein the haplotype comprises at least one marker that is listed in Table A, or is within 1 linkage disequilibrium unit (1 LDU) of a marker listed in Table A; determining whether the haplotype is associated with an increased risk of developing SZ, SPD, or SD; and administering the treatment to the subject if the haplotype indicates that the subject has an increased risk of developing SZ, SPD, or SD.

In another aspect, the invention provides methods for selecting a treatment for administration to a subject. The methods include obtaining a haplotype for the subject, wherein the haplotype comprises at least one marker that is listed in Table A, or is within 1 linkage disequilibrium unit (1 LDU) of a marker listed in Table A; determining whether the haplotype is associated with an increased risk of developing schizophrenia (SZ), schizotypal personality disorder (SPD), or schizoaffective disorder (SD); and administering the treatment for SZ, SPD, or SD to the subject if the haplotype indicates that the subject has an increased risk of developing SZ, SPD, or SD.

In another aspect, the invention provides methods for evaluating the effect of a haplotype on the outcome of a treatment for schizophrenia (SZ), schizotypal personality disorder (SPD), or schizoaffective disorder (SD). The methods include obtaining information regarding outcome of the treatment, wherein the information comprises a parameter relating to the treatment of each subject in a population of subjects; obtaining haplotypes for each subject in the population, wherein the haplotype comprises at least one marker that is listed in Table A, or is within 1 linkage disequilibrium unit (1 LDU) of a marker listed in Table A; and correlating the information regarding outcome with the haplotypes; thereby evaluating the effect of the haplotype on the outcome of the treatment.

In some embodiments, the method includes selecting a treatment for administration to a subject who has a selected haplotype, based on the effect of the haplotype on the outcome of the treatment.

In some embodiments, the information regarding outcome of the treatment is from a completed clinical trial, and the analysis is retrospective.

In another aspect, the invention features methods of predicting a subject's risk of developing SZ, SPD, or SD. The methods include obtaining a reference haplotype. In some embodiments, the reference haplotype is from at least one of the following relatives of the subject: (i) a parent who has SZ, SPD, or SD; (ii) a sibling who has SZ, SPD, or SD, and an unaffected parent; or (iii) a second degree relative (e.g., aunt, uncle, or grandparent) who has SZ, SPD, or SD, and an unaffected parent; obtaining a test haplotype from the subject in the same region; and comparing the test haplotype to a reference haplotype. The sharing of a haplotype in this region between the test haplotype and a reference haplotype from a relative having the disorder is an indication of an increased likelihood that the subject will develop SZ, SPD, or SD. In some embodiments, the reference haplotype is from an unaffected individual, and sharing of a haplotype indicates that there is no increased likelihood that the subject will develop SZ, SD, or SD.

In a further aspect, the invention features methods for detecting the presence of a haplotype associated with susceptibility to SZ, SPD, or SD in a subject, by analyzing a sample of DNA from the subject.

Additionally, the invention features methods of predicting a test subject's risk of developing SZ, SPD, or SD. The methods include obtaining a reference haplotype of a reference subject, wherein the reference subject has SZ, SPD, or SD; determining a test haplotype of the test subject in the same region; and comparing the test haplotype to the reference haplotype, wherein the sharing of a haplotype in this region between the test subject and the reference subject is an indication of an increased likelihood that the test subject will develop SZ, SPD, or SD. In some embodiments, the method further includes comparing the subject's haplotype to a reference subject who does not have SZ, SPD, or SD.

Further, the invention features methods for predicting a test subject's risk of developing SZ. The methods include obtaining a reference haplotype of a reference subject in a region described herein, wherein the reference subject has SZ; obtaining a test haplotype of the test subject in the same region; and comparing the test haplotype to the reference haplotype. The sharing of a haplotype in this region between the test subject and the reference subject is an indication of an increased likelihood that the test subject will develop SZ. In some embodiments, the method also includes comparing the test subject's haplotype to a reference subject who does not have SZ.

In another aspect, the invention features methods for predicting a subject's risk of developing SZ, SPD, or SD. The methods include obtaining genomic DNA (gDNA) from the subject; and determining the absence or presence of a haplotype associated with SZ as described herein. The presence of a haplotype associated with SZ, SPD, or SD indicates that the subject has an increased risk of developing SZ, SD or SPD.

Also provided herein are kits for use in detection of haplotypes associated with SZ, SD or SPD, including at least one nucleic acid probe that hybridizes to a sequence that includes a polymorphism described herein, or can be used to amplify a sequence that includes a polymorphism described herein.

Also provided are arrays that include a substrate having a plurality of addressable areas, wherein one or more of the addressable areas includes one or more probes that can be used to detect a polymorphism described herein.

In another aspect, the invention provides methods for providing information regarding a subject's risk of developing schizophrenia (SZ), schizotypal personality disorder (SPD), or schizoaffective disorder (SD). The methods include obtaining a sample from the subject at a first site; transferring the sample to a second site for analysis, wherein the analysis provides data regarding the identity, presence or absence of at least one test marker that is listed in Table A, or is within 1 LDU of a marker listed in Table A; and transferring the data to one or more of a health care provider, the subject, or a healthcare payer. In some embodiments, the first site is a health care provider's place of business, or is not a health care provider's place of business, e.g., the subject's home.

In some embodiments, the data is transferred to a healthcare payer and used to decide whether to reimburse a health care provider.

Definitions

As used herein, a "haplotype" is one or a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more genetic markers in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs. Chromosome 22 contains about $5.3 \times 10^7$ base pairs (see, e.g., Yunis, Science 191:1268-1270 (1976), and Kavenoff et al., Cold Spring Harbor Symposia on Quantitative Biology 38:1-8 (1973)).

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., $Current\ Protocols\ in\ Molecular\ Biology$, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or haplotypes described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
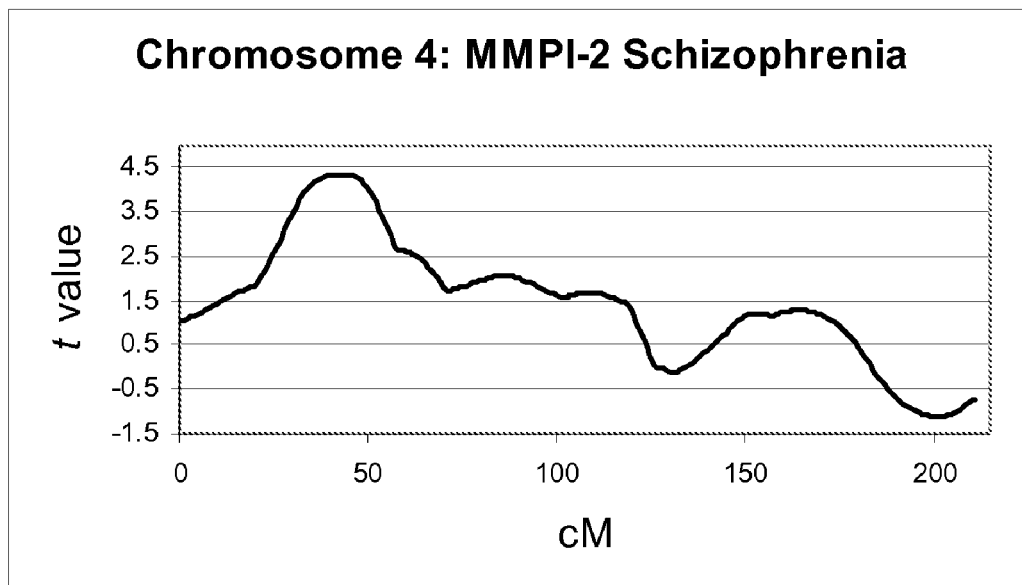
FIG. 1 is a line graph showing the results of QTL linkage analysis for MMPI-2 schizophrenia scale for chromosome 4. Abscissa shows linkage t-values and ordinate shows position along the chromosome in cM. The major peak exceeds the t-value of 4.09 ($P=2.2\times10^{-5}$), the proposed criterion for "significant linkage" for complex genetic traits (Kruglyak and Lander, (1995) Am. J. Hum. Genet. 57: 439-454).

The methods described herein are based, at least in part, on the discovery of haplotypes and markers that are associated with increased risk of having or developing schizophrenia (SZ), schizotypal personality disorder (SPD) or schizoaffective disorder (SD). As described herein, analysis provided evidence of association of the disclosed SNPs and haplotypes with these disorders.

Methods of Diagnoses and Evaluation of Risk

Described herein are a variety of methods for the diagnosis of susceptibility to SZ, SPD or SD. "Susceptibility" does not necessarily mean that the subject will develop SZ, SPD or SD, but rather that the subject is, in a statistical sense, more likely to develop SZ than an average member of the population, i.e., has an increased risk of developing SZ, SPD, or SD. As used herein, susceptibility to SZ exists if the subject has a haplotype associated with an increased risk of SZ, SPD, or SD as described herein. Ascertaining whether the subject has such a haplotype is included in the concept of diagnosing susceptibility to SZ, SPD or SD as used herein. Such determination is useful, for example, for purposes of diagnosis, treatment selection, and genetic counseling. Thus, the methods described herein can include obtaining a haplotype associated with an increased risk of SZ, SPD, or SD as described herein for the subject.

As used herein, "obtaining a haplotype" includes obtaining information regarding the identity, presence or absence of one or more genetic markers in a subject. Obtaining a haplotype can, but need not, include obtaining a sample comprising DNA from a subject, and/or assessing the identity, presence or absence of one or more genetic markers in the sample. The individual or organization who obtains the haplotype need not actually carry out the physical analysis of a sample from a subject; the haplotype can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Obtaining a haplotype can also include or consist of reviewing a subject's medical history, where the medical history includes information regarding the identity, presence or absence of one or more genetic markers in the subject, e.g., results of a genetic test.

In some embodiments, to detect the presence of a haplotype described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for SZ, SPD or SD if the subject has an increased risk of developing SZ, SPD or SD. As another example, a drug or treatment may be indicated for individuals with a certain haplotype, and the insurance company would only reimburse the health care provider (or the insured individual) for prescription or purchase of the drug if the insured individual has that haplotype. The presence or absence of the haplotype in a patient may be ascertained by using any of the methods described herein.

Information gleaned from the methods described herein can also be used to select or stratify subjects for a clinical trial. For example, the presence of a selected haplotype described herein can be used to select a subject for a trial. The information can optionally be correlated with clinical information about the subject, e.g., diagnostic or endophenotypic information.

Haplotypes Associated with SZ, SPD and SD

As described herein, haplotypes associated with SZ, SPD or SD include markers eg. in 4p15.31 (KCNIP4), as exemplified by the transmission disequilibrium results shown in tables 4 and 5; eg. in 4p15.2 (PI4K2B), as exemplified by the transmission disequilibrium results shown in tables 6 and 7; eg. in 22q13.31 (CERK) as exemplified by the transmission disequilibrium results shown in tables 9 and 10; eg. in 22q13.33 (SHANK3) as exemplified by the transmission disequilibrium results shown in tables 11 and 12.

As one example, haplotypes associated with a broader disorder definition including SZ, SPD and SD include one or more markers on chromosomes 4p or 22q that are within 1 linkage disequilibrium unit (1 LDU) of a marker listed in Tables 4, 5, 6, 7, 9, 10, 11 or 12. In some embodiments, the haplotype includes one or more of the markers listed in Tables 4, 5, 6, 7, 9, 10, 11 or 12. Haplotypes associated with a broader disorder definition of SZ can include one or more markers that are within 1 LDU of a marker listed in Tables 4, 5, 6, 7, 9, 10, 11 or 12. In some embodiments, the markers are in a region of 4p15.2 that is between and including SNPs rs313548 and rs313567 at the PI4K2B locus. In some embodiments, the markers are in a region of 4p15.31 between rs6447982 and rs1364836 at the KCNIP4 locus. In some embodiments, the markers are in a region of 22q13.31 between rs801720 and rs710123 at the CERK locus. In some embodiments, the markers are in a region of 22q13.33 between rs713692 and rs756638 at the SHANK3 locus.

As one example, haplotypes associated with a narrow disease definition of SZ include one or more markers on chromosomes 4p or 22q that are within 1 linkage disequilibrium unit (1 LDU) of a marker listed in Tables 4, 5, 6, 7, 9, 10, 11 or 12. Haplotypes associated with a narrower disorder definition of SZ can include one or more markers that are within 1 LDU of a marker listed in Tables 4, 5, 6, 7, 9, 10, 11 or 12. In some embodiments, the markers are in a region of 4p15.2 that is between and including SNPs rs313548 and rs313567 at the PI4K2B locus. In some embodiments, the markers are in a region of 4p15.31 between rs6447982 and rs1364836 at the KCNIP4 locus. In some embodiments, the markers are in a region of 22q13.31 between rs801720 and rs710123 at the CERK locus. In some embodiments, the markers are in a region of 22q13.33 between rs713692 and rs756638 at the SHANK3 locus.

In some embodiments, the gene is KCNIP4, and the rs6447982(A)/rs10016449(T) haplotype is associated with disease. In some embodiments, the gene is PI4K2B, and the rs313548(C) allele is associated with disease. In some embodiments, the gene is CERK, and the rs135667(G)/rs1548977(A) haplotype is associated with disease. In some embodiments, the gene is SHANK3, and the rs9616816(A)-rs6010063(A) haplotype is associated with disease.

In some embodiments, the methods include determining the presence of a haplotype that includes one or more polymorphisms near D22S526 and/or the polymorphisms in the Sult4a1 gene listed in Table 4, and/or polymorphisms within 1 LDU of these markers, e.g., as described in U.S. Pat. Pub. No. 2006-0177851, incorporated herein in its entirety.

SH3 and Multiple Ankyrin Repeat Domains 3 (SHANK3)

SH3 and multiple ankyrin repeat domains 3 (SHANK3, also known as PSAP2; PROSAP2; SPANK-2; and KIAA1650) is a synaptic scaffolding protein that regulates the structural organization of dendritic spines and is a binding partner of proteins known as neuroligins. The human mRNA and protein sequences of SHANK3 are available in GenBank at NM_001080420.1 and NP_001073889.1, respectively. The genomic sequence can be found at NC_000022.9 in Genome Build 36.2 (nucleotides 49459936-49518507 of chromosome 22), with an alternate assembly (based on Celera assembly) at AC_000065.1. For additional information, see also UniGene entry no. Hs.149035 and GeneID: 85358 in the Entrez Gene database. Previously, a role of SHANK3 in autism spectrum disorders has been speculated. See, e.g., Durand et al., Nat. Genet. 39(1):25-7 (2007) [Epub 2006 Dec. 17]

Ceramide Kinase (CERK)

Ceramide kinase (CERK, also known as LK4; hCERK; FLJ21430; FLJ23239; KIAA1646; MGC131878; dA59H18.2; dA59H18.3; and DKFZp434E0211). The human CERK has two isoforms, A and B. The mRNA for isoform A is available in GenBank at NM_022766.4, and the protein is at NP_073603.2. Isoform B is NM_182661.1 (mRNA) and NP_872602.1 (protein) that is developmentally regulated and shows subcellular location-dependent activity. The genomic sequence is NC_000022.9 assembly in Build 36.2, and is at nucleotides 45512816-45458971 of chromosome 22. For additional information see GeneID: 64781 and UniGene: Hs.200668.

Phosphatidylinositol 4-Kinase Type 2 Beta (PI4K2B)

Phosphatidylinositol 4-Kinase Type 2 Beta (PI4K2B, also known as PIK42B; PI4KIIB; and FLJ11105) is an enzyme that can phosphorylate and remove phosphatidylinositol-5-phosphate and may be involved in the response to cellular stress. The human mRNA and protein sequences are in Genbank at NM_018323.2 and NP_060793.1, respectively. The genomic Reference assembly is NC_000004.10 in build 36.2, nucleotides 24844773-24889808 of chromosome 4. See GeneID: 55300 and UniGene Hs.638037 for additional information.

Kv Channel Interacting Protein 4 (KCNIP4)

Kv channel interacting protein 4 (KCNIP4, also known as CALP; KCHIP4; and MGC44947) encodes a member of the family of voltage-gated potassium (Kv) channel-interacting proteins (KCNIPs). Members of the KCNIP family are small calcium binding proteins that are subunit components of native Kv4 channel complexes, and may regulate A-type currents, and thus neuronal excitability, in response to changes in intracellular calcium levels. KCNIP4 also interacts with presenilin. At least 5 alternatively spliced transcript variants encoding distinct isoforms exist for this gene, as follows:

| mRNA GenBank Acc. No. | Protein GenBank Acc. No | Name |
|---|---|---|
| NM_001035003.1 | NP_001030175.1 | Kv channel interacting protein 4 isoform 5 |
| NM_001035004.1 | NP_001030176.1 | Kv channel interacting protein 4 isoform 6 |
| NM_025221.5 | NP_079497.2 | Kv channel interacting protein 4 isoform 1 |
| NM_147182.3 | NP_671711.1 | Kv channel interacting protein 4 isoform 3 |
| NM_147181.3 | NP_671710.1 | Kv channel interacting protein 4 isoform 2 |
| NM_147183.3 | NP_671712.1 | Kv channel interacting protein 4 isoform 4 |

The Reference assembly of the genomic sequence is NC_000004.10, nucleotides 21155377-20339337 of build 36.2 of chromosome 4 are the complement. An alternate assembly (based on the Celera assembly) is at AC_000047.1, nucleotides 21996734-21186744 (complement).

Linkage Disequilibrium Analysis

Linkage disequilibrium (LD) is a measure of the degree of association between alleles in a population. One of skill in the art will appreciate that haplotypes involving markers within 1 Linkage Disequilibrium Unit (LDU) of the polymorphisms described herein can also be used in a similar manner to those described herein. LDUs share an inverse relationship with LD so that regions with high LD (such as haplotype blocks) have few LDUs and low recombination, whilst regions with many LDUs have low LD and high recombination. Methods of calculating LDUs are known in the art (see, e.g., Morton et al., Proc Natl Acad Sci USA 98(9):5217-21 (2001); Tapper et al., Proc Natl Acad Sci USA 102(33):11835-11839 (2005); Maniatis et al., Proc Natl Acad Sci USA 99:2228-2233 (2002)).

Thus, in some embodiments, the methods include analysis of polymorphisms that are within 1 LDU of a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African Americans would ideally be used to identify markers within 1 LDU of a marker described herein for use in genotyping a subject of African American descent.

Exemplary polymorphisms that are within 1 LDU of some of the markers described herein are included in the Examples, e.g., Example 6.

Alternatively, methods described herein can include analysis of polymorphisms that are within a value defined by Lewontin's D' (linkage disequilibrium parameter, see Lewontin, Genetics 49:49-67 (1964)) of a polymorphism described herein. Results can be obtained, e.g., from on line public resources such as HapMap.org. The simple linkage disequilibrium parameter (D) reflects the degree to which alleles at two loci (for example two SNPs) occur together more often (positive values) or less often (negative values) than expected in a population as determined by the products of their respective allele frequencies. For any two loci, D can vary in value from −0.25 to +0.25. However, the magnitude of D (Dmax) varies as function of allele frequencies. To control for this, Lewontin introduced the D' parameter, which is D/Dmax and varies in value from −1 (alleles never observed together) to +1 (alleles always observed together). Typically, the absolute value of D' (i.e., |D'|) is reported in online databases, because it follows mathematically that positive association for one set of alleles at two loci corresponds to a negative association of equal magnitude for the reciprocal set. This disequilibrium parameter varies from 0 (no association of alleles at the two loci) to 1 (maximal possible association of alleles at the two loci).

Thus, in some embodiments, the methods include analysis of polymorphisms that are within D'>0.75, or D'=1, for pairwise comparisons, of a polymorphism described herein.

Identification of Additional Markers for Use in the Methods Described Herein

In general, genetic markers can be identified using any of a number of methods well known in the art. For example, numerous polymorphisms in the regions described herein are known to exist and are available in public databases, which can be searched using methods and algorithms known in the art. Alternately, polymorphisms can be identified by sequencing either genomic DNA or cDNA in the region in which it is desired to find a polymorphism. According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence, or the "affected" sequence. In some embodiments, a reference sequence can be from, for example, the human draft genome sequence, publicly available in various databases, or a sequence deposited in a database such as GenBank. In some embodiments, the reference sequence is a composite of ethnically diverse individuals.

In general, if sequencing reveals a difference between the sequenced region and the reference sequence, a polymorphism has been identified. The fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms, such as insertions and deletions, may have more than four alleles.

Other Genetic Markers of Schizophrenia

The methods described herein can also include determining the presence or absence of other markers known or suspected to be associated with SZ, or with SZ, SD or SPD, e.g., markers outside of a region identified herein, see, e.g., Harrison and Owen, Lancet, 361(9355):417-419 (2003), including, for example, markers on chromosome 22 and other chromosomes, e.g., in the region of 22q12.3 (e.g., near D22S283), 22q11.2, 22q11.2, 22q11-q13, 1q42.1, 1q42.1, 4p, 18p, 15q15, 14q32.3, 13q34, 13q32, 12q24, 11q14-q21, 1q21-q22, 10p15-p13 (e.g., near D10S189), 10q22.3, 8p12-21, 6q13-q26, 6p22.3, 6p23, 5q11.2-q13.3, and/or 3p25. In some embodiments, the methods include determining the presence or absence of one or more other markers that are or may be associated with SZ, or with SZ, SD or SPD, e.g., in one or more genes, e.g., ACE (Illi et al., Eur Neuropsychopharmacol 13:147-151 (2003)); ADRA1A (Clark et al., Biol Psychiatry. 58(6):435-9 (2005)); ADH1B (Xu et al., Mol. Psychiatry. 9(5):510-21 (2004); Vawter et al., Hum Genet. 119(5):558-70 (2006)); AHI1 (Eur J Hum Genet. 14(10):1111-9 (2006)); AKT1 (Emamian et al., Nature Genet. 36:131-137 (2004)); ALDH3B1 (Sun et al. Sci. China C. Life. Sci. 48(3):263-9 (2005)); ALK (Kunagi et al., J Neural Transm. 113(10):1569-73 (2006)); APC (Cui et al., Mol Psychiatry (7):669-77 (2005)); APOE (Liu et al., Schizophr Res 62: 225-230 (2003)); ARSA (Marcao et al., Mol Genet Metab. 79(4): 305-7 (2003); ARVCF (Chen et al., Schizophr Res. 72(2-3): 275-7 (2005)); ATXN1 (Pujana et al Hum Genet 99:772-775 (1997); Joo et al., Psychiatr Genet 9:7-11 (1999); Fallin et al., Am J Hum Genet 77:918-936 (2005)); BDNF (Neves-Pereira et al., Molec. Psychiat. 10:208-212 (2005)); BRD1 (Severinsen et al., Mol Psychiatry. 11(12):1126-38 (2006)); BZRP (Kurumaji et al., J Neural Transm. 107(4):491-500 (2000)); DAO (Owen et al., Trends Genet. 21(9):518-25 (2005)); DAOA (Owen et al., 2005, supra); CAPON (Brzustowicz et al., Am J Hum Genet. 74(5):1057-63 (2004)); CCKAR (Zhang et al., Mol Psychiatry 5:239-240 (2000); Sanjuan et al., Eur Psychiatry 19:349-353 (2004)); CHGB (Kitao et al., Psychiatr Genet. 10:139-143 (2000); Zhang et al., Neurosci Lett 323:229-233 (2002)); CHI3L1 (Zhao et al., Am J Hum Genet. 80(1):12-8 (2007)); CHRNA2 (Blayeri et al., Europ. J. Hum. Genet. 9: 469-472 (2001)); CHRNA7 (Leonard et al. Arch Gen Psychiatry. 2002 59:1085-1096 (2002); De Luca et al. Neuropsychobiology. 50:124-127 (2004)); CLDN5 (Sun et al., Eur Psychiatry 19:354-357 (2004); Wei and Hemmings, Prostaglandins Leukot Essent Fatty Acids 73(6)4:41-445 (2005)); COMT (Shifman et al., Am. J. Hum. Genet. 71:1296-1302 (2002)); CNR1 (Ujike et al., Mol Psychiatry 7:515-518 (2002)); CPLX2 (Lee et al., Behav Brain Funct. 1:15 (2005)); DGCR8 (Jacquet et al., Hum Mol. Genet. 11(19):2243-9 (2002)); DISC1 (Owen et al., 2005, supra; see, e.g., the D1S2709 marker (Ekelend et al., Hum. Molec. Genet. 10:1611-1617 (2001), DDR1 (Roig et al., Mol Psychiatry. 2007 Apr. 17; [Epub ahead of print]); DRD4 (Lung et al., Schizophr Res 57:239-245 (2002)); DDR3 (Williams et al., Mol Psychiatry 3:141-149 (1998)); DRD5 (Williams et al., Psychiatr Genet. 7:83-85 (1997); Muir et al., Am J Med Genet 105:152-158 (2001)); HEP3 haplotype, Hennah et al., Hum. Molec. Genet. 12: 3151-3159 (2003), and Leu607Pro, Hodgkinson et al., Am. J. Hum. Genet. 75:862-872 (2004), Erratum: Am. J. Hum. Genet. 76:196 (2005)); DISC2 (Millar et al., Ann Med. 36(5):367-78 (2004)); DPYSL2 (Hong et al., Am J Med Genet B Neuropsychiatr Genet. 136(1):8-11 (2005)); DRD1 (Coon et al., Am. J. Hum. Genet. 52: 327-334

(1993)); DRD2 (Glatt et al., Am. J. Psychiat. 160:469-476 (2003)); DRD3 (Rybakowski et al., Molec. Psychiat. 6:718-724 (2001)); DTNBP1 (Owen et al., 2005, supra); EGR3 (Yamada et al., Proc Natl Acad Sci 104(8):2815-20 (2007)); EPSIN4 (Am J Hum Genet. 76(5):902-7 (2005)); ErbB; EGF (Futamura et al., Am. J. Hum. Genet. 52: 327-334 (2002)); ENTH (Pimm et al., Am J Hum Genet. 76:902-907 (2005); Tang et al., Mol Psychiatry 11:395-399 (2006)); ERBB4 (Norton et al., Am J Med Genet B Neuropsychiatr Genet 14; 11; 96-101 (2005); Silberberg et al., Am J Med Genet B Neuropsychiatr Genet 141B; 2; 142-148 (2006)); FEZ1 (Yamada et al., Biol Psychiatry 56:683-690(2004)); FOXP2 (Sanjuan et al., Psychiatr Genet. 16(2):67-72 (2006)); FXYD6 (Choudhury et al., Am J Hum Genet. 80(4):664-72 (2007)); FZD3 (Katsu et al., Neurosci Lett 353:53-56 (2003); Yang et al., Biol Psychiatry 54:1298-1301 (2003); Zhang et al., Am J Med Genet 129B:16-19 (2004)); GABRA1, GABRA2, GABRA6, GABRP (Petryshen et al., Mol Psychiatry. 10(12):1057 (2005)); GABBR1 (Zai et al. Eur Neuropsychopharmacol. 15:347-52 (2005); Le-Niculescu et al. Am J Med Genet B Neuropsychiatr Genet. 144:129-58 (2007)); GAD1 (Addington et al., Mol Psychiatry 10:581-588 (2005)); GFRA1 (Semba et al., Brain Res Mol Brain Res. 124(1):88-95 (2004)); GCLM (Tosic et al., Am J Hum Genet. 79(3):586-92 (2006)); GNB3 (Kunugi et al., J. Neural Transm. 109(2):213-8 (2002)); GPR78 (Underwood et al., Mol Psychiatry. 11(4):384-94 (2006)); GRIA1 (Magri et al., Am J Med Genet B Neuropsychiatr Genet 141(3):287-93 (2006)); GNPAT (Lin et al., Biol Psychiatry. 60(6):554-62 (2006)); GRID1 (Fallin et al., Am J Hum Genet 77:918-936 (2005)); GRIK1 (Shibata et al., Psychiatr Genet. 11(3):139-44 (2001)); GRIK2 (Shibata et al., Psychiatry Res. 113(1-2): 59-67 (2002)); GRIK3 (Shibata et al., Psychiatry Res. 30: 141(1): 39-51 (2006)); GRIK4 (Pikard et al., Mol Psychiatry 11(9):847-57 (2006)); GRIN1 (Qin et al., Eur J Hum Genet. 13(7):807-14 (2005)); GRIN2A, GRIN2B (Abdolmaleky et al., Am J Pharmacogenomics. 5(3):149-60 (2005)); GRIN2D (Makino et al., Psychiatr Genet. 15(3):215-21 (2005)); GRM3 (Egan et al., Proc Natl Acad Sci USA. 101(34):12604-9 (2004)); GRM4 (Ohtsuki et al., Psychiatr Genet. 11(2):79-83 (2001)); GRM5 (Devon et al., Mol Psychiatry. 6(3):311-4 (2001)); GSTM1 (Harada et al., Biochem Biophys Res Commun 281:267-271 (2001); Pae et al., Psychiatr Genet 14:147-150 (2004)); G30/G72 (Schulze et al., Am J Psychiatry. 162(11):2101-8 (2005)); HTR2A (Baritaki et al., Eur J Hum Genet. 12(7):535-41 (2004)); HLA-DRB1 (Schwab et al., Am J Med Genet. 114(3):315-20 (2002)); HLA-BRB3 (Yu et al., Zhonghua Liu Xing Bing Xue Za Zhi. 24(9):815-8 (2003)); HTR5A (Abdolmaleky et al., Schizophr Res 67:53-62 (2004)); HTR6 (Tsai et al., Neurosci Lett. 271 (2):135-7 (1999)); IL1B (Katila et al., Mol Psychiatry 4:179-181 (1999); Meisenzahal et al., Am J Psychiatry 158:1316-1319 (2001); Zanardini et al., J Psychiatr Res 37:457-462 (2003)); IL1RN (Zanardini et al., J Psychiatr Res 37:457-462 (2003); Kim et al., Psychiatr Genet 14:165-167 (2004); Papiol et al., Neuroimage 27:1002-1006 (2005)); IL10 (Chiavetto et al., Biol Psychiatry 51:480-484 (2002); Jun et al., Psychiatry Clin Neurosci 56:177-180 (2002)); IL2RB (Schwab et al., Am J Med Genet. 60(5):436-43 (1995)); KCNN3 (Ujike et al., Psychiatry Res. 101(3):203-7 (2001)); KIF13A (Jamain et al., Genomics. 74(1):36-44 (2001)); KIF2A (Li et al., Neurosci Letters 407(2) 151-5 (2006)); KPNA3 (Wei and Hemmings, Neurosci Res. 52(4):342-6 (2005)); LGI1 (Fallin et al. A J Hum Genet. 77:918-36 (2005)); MAG (Wan et al., Neurosci Lett. 388(3):126-31 (2005)); MAOA (Jonsson et al., Schizophr Res 61:31-37 (2003); Wei and Hemmings. Psychiatr Genet. 9, 177-181 (1999)); MED12 (Sandhu et al., Am J Med Genet B Neuropsychiatr Genet. 123B: 33-38 (2003); Spinks et al., Am J Med Genet B Neuropsychiatr Genet. 127B:20-27 (2004)); MLC1 (Verma et al., Biol Psychiatry. 58(1):16-22 (2005)); MTHFR (Lewis et al., Am. J. Med. Genet. (Neuropsychiat. Genet.) 135B:2-4 (2005)); MTR (Kempisty et al., Psychiatr Genet. 17(3):177-81 (2007)); MTHFD1 (Kempisty et al., Psychiatr Genet. 17(3):177-81 (2007)); NCAM1 (Sullivan et al., Biol Psychiatry. 61(7):902-10 (2007)); NDE1 (Hennah et al., Hum Mol Genet. 16(5):453-62 (2006)); NDUFV2 (Waskizuka et al., Am J Med Genet B Neuropsychiatr Genet. 141(3):301-4 (2006)); NOS1 (Liou et al., Schizophr Res. 65(1):57-9 (2003)); NOTCH4 (Wei and Hemmings, (Letter) Nature Genet. 25:376-377 (2000)); NPAS3 (Kamnasaran et al., J Med Genet. 40:325-332 (2003)); NRG1 (Owen et al., 2005, supra); NRG3 (Fallin et al. A J Hum Genet. 77:918-36 (2005)); NTNG1 (Fukawasa et al., J Med Dent Sci 51:121-128 (2004); Aoki-Suzuki et al., Biol Psychiatry 57:382-393 (2005)); NTNG2 (Aoki-Suzuki et al., Biol Psychiatry 57:382-393 (2005)); NTF3 (Jonsson et al., Acta Psychiatr Scand 95:414-419 (1997)); OLIG2 (Georgieva et al., Proc Natl Acad Sci 103(33):12469-74 (2006)); PCQAP (Sandhu et al., Psychiatr Genet. 14(3):169-72 (2004)); PDE4B (Millar et al., Science 310:1187-1191 (2005)); PDLIM5 (Horiuchi et al., Biol Psychiatry 59(5):434-9 (2005)); PICK1 (Hong et al., Neuroreport 15:1965-1967 (2004); Fujii et al., Molecular Psychiatry 11:150-157 (2005)); PIK3C3 (Stopkova et al., Biol Psychiatry 55:981-988 (2004); Duan et al., Neurosci Lett., 379:32-36 (2005)); PIK4CA (Saito et al., Am J Med Genet B Neuropsychiatr Genet. 116(1):77-83 (2003)); PIP5K2A (Stopkova et al., Psychiatr Genet. 15(3): 223-7 (2005)); PLA2G4A, PLA2G4C (Yu et al., Prostaglandins Leukot Essent Fatty Acids. 73(5):351-4 (2005)); PLA2G4B (Tao et al., Am J Med Genet B Neuropsychiatr Genet 137:56-58 (2005)); PLXNA2 (Mah et al., Molecular Psychiatry 11:471-478 (2006)); PTGS2 (Wei and Hemmings. Prostaglandins Leukot Essent Fatty Acids 70:413-415 (2004)); PPP3CC (Gerber et al., Proc Natl Acad Sci USA. 100(15): 8993-8 (2003)); PNOC (Blayeri et al., 2001); PRODH (Chakravarti, Proc. Nat. Acad. Sci. 99:4755-4756 (2002)); QKI (Aberg et al., Am J Med Genet B Neuropsychiatr Genet. 2005 Dec. 9; [Epub ahead of print]); RGS4 (Chowdari et al., Hum. Molec. Genet. 11:1373-1380 (2002), Erratum: Hum. Molec. Genet. 12:1781 (2003)); RELN (Costa et al., Mol Interv. 2(1):47-57 (2002)); RTN4 (Novak et al., Brain Res Mol Brain Res 107:183-189 (2002); Tan et al., Brain Res Mol Brain Res 139:212-216 (2005)); SCAT (Culkjovic et al., Am J Med. Genet. 96(6):884-7 (2000)); SLC15A1 (Maheshwari et al., BMC Genomics. 3(1):30 (2002)); SLC18A1 (Bly, Schizophr Res. 78(2-3):337-8 (2005)); SLC18A2 (Gutierrez et al. Am J Med Genet B Neuropsychiatr Genet. 144(4):502-7 (2007)); SLC6A4 (Fan and Sklar, Mol Psychiatry. 10(10): 928-38, 891 (2005)); SNAP29 (Saito et al., Mol Psychiatry 6(2):193-201 (2001); Erratum in: Mol Psychiatry 6(5):605 (2001); SULT4A1 (Brennan and Chondra. Am J Med Genet B Neuropsychiatr Genet. 139(1):69-72 (2005)); SYNGR1 (Verma et al., Biol Psychiatry. 55(2):196-9 (2004)); SYN2 (Chen et al., Bio. Psychiat. 56:177-181 (2004)); SYN3 (Porton et al. Biol Psychiatry. 55(2):118-25 (2004)); TAAR4 (Duan et al., Am J Hum Genet 75:624-638 (2004)); TBP/SCA17 (Chen et al., Schizophr Res. 78(2-3):131-6 (2005)); TH (Kurumaji et al., J Neural Transm 108:489-495 (2001); Meloni et al., C R Acad Sci III 318:803-809 (1995)); TNFA (Morar et al., Am J Med Genet B Neuropsychiatr Genet. 144(3):318-24 (2007)); TPH1 (Nolan et al., Psychiatr Genet 10:109-115 (2000); Hong et al., Schizophr Res 49:59-63 (2001); Sekizawa et al., Am J Med Genet B Neuropsychiatr Genet. 128:24-26 (2004)); TPP2 (Fallin et al. A J Hum Genet. 77:918-36 (2005)); TPS3 (Park et al., Schizophr Res 67:71-74 (2004); Ni et al., Neurosci Lett 388:173-178 (2005)); TRAR4 (Am J Hum Genet. 75(4):624-38 (2004)); TRAX (Thomson et al., Mol Psychiatry. 10(7):657-68, 616 (2005)); UFD1L (De Luca et al., Am J Med Genet. 105(6):529-33 (2001)); UCP2 (Yasuno et al., Am J Med Genet B Neuropsychiatr Genet. 144(2):250-3 (2007)); UCP4 (Yasuno et al.,: Am J Med Genet B Neuropsychiatr Genet. 144(2):250-3 (2007)); UHMK1 (Puri et al., Biol Psychiatry 61(7):873-9 (2007)); XBP1 (Chen et al., Biochem Biophys Res Commun 319:866-870 (2004); Kakiuchi et al., Psychiatry Clin Neurosci 58:438-440 (2004));YWHAH (Toyooka et al., Am J Med Genet. 88(2):164-7 (1999)); ZDHHC8 (Mukai et al., Nature Genet. 36:725-731 (2004)); or ZNF74 (Takase et al., Schizophr Res. 52(3):161-5 (2001)). See also, e.g., OMIM entry no. 181500 (SCZD).

In some embodiments, the methods described herein can include determining the presence or absence of a haplotype associated with SZ, SPD or SD, as described in U.S. Pat. Pub. No. 2006-0177851, the entire contents of which are incorporate herein by reference. For example, the haplotype can include one or more markers in a region of 22q13 that is between and including SNPs rs738596 on the proximal end, and rs137853 on the distal end. For example, the haplotype can include marker D22S526, and/or a polymorphism of Sulfotransferase 4A1 (Sult4a1), e.g., one or more of rs138060, rs138097, rs138110, or D22s1749e.

Methods of Determining the Presence or Absence of a Haplotype Associated with SZ, SPD or SD The methods described herein include determining the presence or absence of haplotypes associated with SZ, SPD or SD. In some embodiments, an association with SZ is determined by the presence of a shared haplotype between the subject and an affected reference individual, e.g., a first or second-degree relation of the subject, and the absence of the haplotype in an unaffected reference individual. Thus the methods can include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a haplotype associated with SZ, SPD or SD as described herein can be determined using methods known in the art, e.g., gel electrophoresis, capillary electrophoresis, size exclusion chromatography, sequencing, and/or arrays to detect the presence or absence of the marker(s) of the haplotype. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the methods described herein include determining the sequence of the entire region of the PI4K2B locus described herein as being of interest, e.g., between and including SNPs rs313548 and rs313567. In some embodiments, the methods described herein include determining the sequence of the entire region of the KCNIP4 locus described herein as being of interest, e.g., between and including SNPs rs6447982 and rs1364836. In some embodiments, the methods described herein include determining the sequence of the entire region of the CERK locus described herein as being of interest, e.g., between and including SNPs rs801720 and rs710123. In some embodiments, the methods described herein include determining the sequence of the entire region of the SHANK3 locus described herein as being of interest, e.g., between and including SNPs rs713692 and rs756638. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications,* 1:17 (1991); PCR (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a haplotype as described herein. The haplotype can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of SZ.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to SZ.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to SZ) to DNA from the subject is indicative of susceptibility to SZ.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997). The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1\times10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein. In some embodiments, the probe can hybridize to a target sequence within a region delimited by SNP rs313548 and SNP rs313567 (described on the internet at ncbi.nlm.nih.gov/SNP/snp_ref.cgi?rs=313548 and ncbi.nlm.nih.gov/SNP/snp_ref.cgi?rs=313567, respectively). In some embodiments, the probe can hybridize to a target sequence within a region delimited by SNP rs6447982 and SNP rs1364836 (described on the internet at ncbi.nlm.nih.gov/SNP/snp_ref.cgi?rs=6447982 and ncbi.nlm.nih.gov/SNP/snp_ref.cgi?rs=1364836, respectively). In some embodiments, the probe can hybridize to a target sequence within a region delimited by SNP rs801720 and SNP rs710123 (described on the internet at ncbi.nlm.nih.gov/SNP/snp_ref.cgi?rs=rs801720 and ncbi.nlm.nih.gov/SNP/snp_ref.cgi?rs=rs710123, respectively). In some embodiments, the probe can hybridize to a target sequence within a region delimited by SNP rs713692 and SNP rs756638 (described on the internet at ncbi.nlm.nih.gov/SNP/snp_ref.cgi?rs=rs713692 and ncbi.nlm.nih.gov/SNP/snp_ref.cgi?rs=rs756638, respectively).

In some embodiments, the probe can bind to another marker sequence associated with SZ, SPD or SD, as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^3H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence comprising a polymorphism listed in Table A, and can be used to detect the absence or presence of said polymorphism, e.g., one or more SNPs, microsatellites, minisatellites, or indels, as described herein, to determine a haplotype. For example, the array can include one or more nucleic acid probes that can be used to detect a polymorphism listed in Table A. In some embodiments, the array further includes at least one area that includes a nucleic acid probe that can be used to specifically detect another marker associated with SZ, SPD or SD, as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments. Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 4p and/or 22q, e.g., a region between SNP rs801720 and SNP rs710123, e.g., a region between SNP rs713692 and rs756638, optionally, a different portion of genomic DNA, e.g., a portion that includes a different portion of human chromosomes 22 and/or 4, or another chromosome, e.g., including another region associated with SZ, SPD or SD., and detecting binding of a nucleic acid from the sample to the array. Optionally, the method includes amplifying nucleic acid from the sample, e.g., genomic DNA that includes a portion of a human chromosome described herein, and, optionally, a region that includes another region associated with SZ, SPD, or SD, prior to or during contact with the array.

In some aspects, the methods described herein can include using an array that can ascertain differential expression patterns or copy numbers of one or more genes in samples from normal and affected individuals (see, e.g., Redon et al., Nature. 444(7118):444-54 (2006)). For example, arrays of probes to a marker described herein can be used to measure polymorphisms between DNA from a subject having SZ, SPD, or SD, and control DNA, e.g., DNA obtained from an individual that does not have SZ, SPD, or SD, and has no risk factors for SZ, SPD, or SD. Since the clones on the array contain sequence tags, their positions on the array are accurately known relative to the genomic sequence. Different hybridization patterns between DNA from an individual afflicted with SZ, SPD or SD and DNA from a normal individual at areas in the array corresponding to markers in human chromosome 4p and/or 22q as described herein, and, optionally, one or more other regions associated with SZ, SPD, or SD, are indicative of a risk of SZ. Methods for array production, hybridization, and analysis are described, e.g., in Snijders et al., (2001) *Nat. Genetics* 29:263-264; Klein et al., (1999) Proc. Natl. Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002. Real time quantitative PCR can also be used to determine copy number.

In another aspect, the invention features methods of determining the absence or presence of a haplotype associated with SZ as described herein, using an array described above. The methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for SZ, and comparing the binding of the first sample with one or more references, e.g., binding of a sample from a subject who is known to have SZ, SPD, or SD, and/or binding of a sample from a subject who is unaffected, e.g., a control sample from a subject who neither has, nor has any risk factors for SZ, SPD, or SD. In some embodiments, the methods include contacting the array with a second sample from a subject who has SZ, SPD or SD; and comparing the binding of the first sample with the binding of the second sample. In some embodiments, the methods include contacting the array with a third sample from a cell or subject that does not have SZ and is not at risk for SZ; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Schizophrenia, Schizotypal Personality Disorder, and Schizoaffective Disorder

The methods described herein can be used to determine an individual's risk of developing schizophrenia (SZ), schizotypal personality disorder (SPD), and/or a schizoaffective disorder (SD).

Schizophrenia (SZ)

SZ is considered a clinical syndrome, and is probably a constellation of several pathologies. Substantial heterogeneity is seen between cases, which is thought to reflect multiple overlapping etiologic factors, including both genetic and environmental contributions. A diagnosis of SZ is typically indicated by chronic psychotic symptoms, e.g., hallucinations and delusions. Disorganization of thought and behavior are common and are considered distinguishing factors in the diagnosis of SZ. Patients typically have some subtle impairments in cognition. Reduced emotional experience and expression, low drive, and impaired speech are observed in a subgroup of patients. Cognitive, emotional and social impairments often appear early in life, while the psychotic symptoms typically manifest in late adolescence or early adulthood in men, a little later in women.

A diagnosis of SZ can be made according to the criteria reported in the *Diagnostic and Statistical Manual of Mental Disorders, Fourth Edition, Text Revision*, American Psychiatric Association, 2000, (referred to herein as DSM-IV) as follows:

Diagnostic Criteria for SZ

All six criteria must be met for a diagnosis of SZ.

A. Characteristic symptoms: Two (or more) of the following, each present for a significant portion of time during a one month period (or less if successfully treated):

(1) delusions
(2) hallucinations
(3) disorganized speech (e.g., frequent derailment or incoherence)
(4) grossly disorganized or catatonic behavior
(5) negative symptoms, e.g., affective flattening, alogia, or avolition Only one criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder Exclusion: Schizoaffective Disorder and Mood Disorder With Psychotic Features have been ruled out because either (1) no major depressive, manic, or mixed episodes have occurred concurrently with the active-phase symptoms; or (2) if mood episodes have occurred during active-phase symptoms, their total duration has been brief relative to the duration of the active and residual periods.

E. Substance/General Medical Condition Exclusion: The disturbance is not due to the direct physiological effects of a substance (e.g., a drug of abuse, a medication) or a general medical condition.

F. Relationship to a Pervasive Developmental Disorder: If the patient has a history of Autistic Disorder or another Pervasive Developmental Disorder, the additional diagnosis of SZ is made only if prominent delusions or hallucinations are also present for at least a month (or less if successfully treated).

Schizoaffective Disorder (SD)

SD is characterized by the presence of affective (depressive or manic) symptoms and schizophrenic symptoms within the same, uninterrupted episode of illness.

Diagnostic Criteria for Schizoaffective Disorder

The DSM-IV Criteria for a diagnosis of schizoaffective disorder is as follows:

An uninterrupted period of illness during which, at some time, there is either (1) a Major Depressive Episode (which must include depressed mood), (2) a Manic Episode, or (3) a Mixed Episode, concurrent with symptoms that meet (4) Criterion A for SZ, above.

A. Criteria for Major Depressive Episode

At least five of the following symptoms must be present during the same 2-week period and represent a change from previous functioning; at least one of the symptoms is either (1) depressed mood or (2) loss of interest or pleasure.

(1) depressed mood most of the day, nearly every day, as indicated by either subjective report (e.g., feels sad or empty) or observation made by others (e.g., appears tearful). In children and adolescents, this can be an irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. (In children, failure to make expected weight gains is considered).

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day (either by subjective account or as observed by others)

(9) recurrent thoughts of death (not just fear of dying), recurrent suicidal ideation without a specific plan, or a suicide attempt or a specific plan for committing suicide In addition, the symptoms do not meet criteria for a Mixed Episode. The symptoms cause clinically significant distress or impairment in social, occupational, or other important areas of functioning. The symptoms are not due to the direct physiological effects of a substance (e.g., a drug of abuse, a medication) or a general medical condition (e.g., hypothyroidism).

The symptoms are not better accounted for by Bereavement, i.e., after the loss of a loved one, the symptoms persist for longer than 2 months, or are characterized by marked functional impairment, morbid preoccupation with worthlessness, suicidal ideation, psychotic symptoms, or psychomotor retardation.

B. Criteria for Manic Episode

A manic episode is a distinct period of abnormally and persistently elevated, expansive, or irritable mood, lasting at least one week (or any duration, if hospitalization is necessary).

During the period of mood disturbance, three (or more) of the following symptoms have persisted (four if the mood is only irritable) and have been present to a significant degree:

(1) inflated self-esteem or grandiosity
(2) decreased need for sleep (e.g., feels rested after only 3 hours of sleep)
(3) more talkative than usual or pressure to keep talking
(4) flight of ideas or subjective experience that thoughts are racing
(5) distractibility (i.e., attention too easily drawn to unimportant or irrelevant external stimuli)
(6) increase in goal-directed activity (either socially, at work or school, or sexually) or psychomotor agitation
(7) excessive involvement in pleasurable activities that have a high potential for painful consequences (e.g., engaging in unrestrained buying sprees, sexual indiscretions, or foolish business investments)

The symptoms do not meet criteria for a Mixed Episode. The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

C. Criteria for Mixed Episode

A mixed episode occurs when the criteria are met both for a Manic Episode and for a Major Depressive Episode (except for duration) nearly every day during at least a 1-week period. The mood disturbance is sufficiently severe to cause marked impairment in occupational functioning or in usual social activities or relationships with others, or to necessitate hospitalization to prevent harm to self or others, or there are psychotic features.

The symptoms are not due to the direct physiological effects of a substance (e.g., a drug of abuse, a medication, or other treatment) or a general medical condition (e.g., hyperthyroidism).

D. Criterion A of SZ

See above.

E. Types of SD

The type of SD may be may be specifiable, as either Bipolar Type, if the disturbance includes a Manic or a Mixed Episode (or a Manic or a Mixed Episode and Major Depressive Episodes), or Depressive Type, if the disturbance only includes Major Depressive Episodes.

F. Associated Features

Features associated with SD include Learning Problems, Hypoactivity, Psychotic, Euphoric Mood, Depressed Mood, Somatic/Sexual Dysfunction, Hyperactivity, Guilt/Obsession, Odd/Eccentric/Suspicious Personality, Anxious/Fearful/Dependent Personality, and Dramatic/Erratic/Antisocial Personality.

Schizotvpal Personality Disorder (SPD)

Diagnostic Criteria for SPD

A diagnosis of SPD under the criteria of the DSM-IV is generally based on a pervasive pattern of social and interpersonal deficits marked by acute discomfort with, and reduced capacity for, close relationships as well as by cognitive or perceptual distortions and eccentricities of behavior, beginning by early adulthood and present in a variety of contexts, as indicated by five (or more) of the following:

(1) ideas of reference (excluding delusions of reference)

(2) odd beliefs or magical thinking that influences behavior and is (3) inconsistent with subcultural norms (e.g., superstitiousness, belief in clairvoyance, telepathy, or "sixth sense;" in children and adolescents, bizarre fantasies or preoccupations)

(4) unusual perceptual experiences, including bodily illusions (5) odd thinking and speech (e.g., vague, circumstantial, metaphorical, overelaborate, or stereotyped)

(6) suspiciousness or paranoid ideation (7) inappropriate or constricted affect (8) behavior or appearance that is odd, eccentric, or peculiar (9) lack of close friends or confidants other than first-degree relatives

(10) excessive social anxiety that does not diminish with familiarity and tends to be associated with paranoid fears rather than negative judgments about self SPD is diagnosed if the symptoms do not occur exclusively during the course of SZ, a Mood Disorder With Psychotic Features, another Psychotic Disorder, or a Pervasive Developmental Disorder, and the disturbance is not due to the direct physiological effects of a substance (e.g., a drug of abuse, a medication) or a general medical condition.

Associated features of SPD include Depressed Mood and Odd/Eccentric/Suspicious Personality.

Endophenotypes in SZ

A number of endophenotypes, i.e., intermediate phenotypes, that may more closely reflect biological mechanisms behind SZ, have been suggested, such as prepulse inhibition, structural abnormalities evident in MRI scans, specific domains of cognition (e.g., executive function), fine motor performance, working memory, etc.

Endophenotypes can also include clinical manifestations such as hallucinations, paranoia, mania, depression, obsessive-compulsive symptoms, etc., as well as response or lack of response to drugs and comorbidity for substance and alcohol abuse.

See, e.g., Kendler et al., Am J Psychiatry 152(5):749-54 (1995); Gottesman and Gould, Am J Psychiatry 160(4):636-45 (2003); Cadenhead, Psychiatric Clinics of North America. 25(4):837-53 (2002); Gottesman and Gould, American Journal of Psychiatry. 160(4):636-45 (2003); Heinrichs, Neuroscience & Biobehavioral Reviews. 28(4):379-94 (2004); and Zobel and Maier, Nervenarzt. 75(3):205-14 (2004).

There is now evidence that some candidate genes that were identified using DSM-IV type categorical definitions for "affected" individuals may influence specific endophenotypes, see, e.g., Baker et al., Biol Psychiatry 58(1):23-31 (2005); Cannon et al., Arch Gen Psychiatry 62(11):1205-13 (2005); Gothelf et al., Nat Neurosci 8(11):1500-2 (2005); Hallmayer et al., Am J Hum Genet 77(3):468-76 (2005); Callicott et al., Proc Natl Acad Sci USA 102(24):8627-32 (2005); Gornick et al., J Autism Dev Disord 1-8 (2005). Thus, the methods described herein can be used to associate haplotypes of 22q13 with specific endophenotypes.

Current Treatment of SZ, SD, or SPD

Subjects with SZ typically require acute treatment for psychotic exacerbations, and long-term treatment including maintenance and prophylactic strategies to sustain symptom improvement and prevent recurrence of psychosis. Subjects with schizoaffective disorder experience the symptoms of both SZ and affective disorder (manic and/or depressive), thus require the specific treatments for each disorder. Subjects with SPD sometimes require medication for acute psychotic episodes but are often treated using psychosocial methods. The methods described herein can include the administration of one or more accepted or experimental treatment modalities to a person identified as at risk of developing SZ, SPD, or a SD, based on the presence of a haplotype associated with SZ, SPD, or SD. Currently accepted treatments presently include both pharmacologic and psychosocial management, and occasionally electroconvulsive therapy (ECT).

Standard pharmacologic therapies for SZ and SD include the administration of one or more antipsychotic medications, which are typically antagonists acting at postsynaptic $D_2$ dopamine receptors in the brain. Antipsychotic medications include conventional, or first generation, antipsychotic agents, which are sometimes referred to as neuroleptics because of their neurologic side effects, and second generation antipsychotic agents, which are less likely to exhibit neuroleptic effects and have been termed atypical antipsychotics.

In some embodiments, the methods described herein include the administration of one or more antipsychotic medications to a person identified by a method described herein as being at risk of developing SZ, SPD, or SD. Antipsychotic medications substantially reduce the risk of relapse in the stable phase of illness. In some embodiments, the methods include the administration of a first generation antipsychotic medication at a dose that is around the "extrapyramidal symptom (EPS) threshold" (i.e., the dose that will induce extrapyramidal side effects, e.g., bradykinesia, rigidity, or dyskinesia, with minimal rigidity detectable on physical examination, and/or a second-generation antipsychotics at a dose that is therapeutic, yet below the EPS threshold.

Standard pharmacologic therapies for SD also include the administration of a combination of antidepressant, and anti-anxiety medication. Suitable antidepressants include serotonergic antidepressants, e.g., fluoxetine or trazodone. Suitable anxiolytics include benzodiazepines, e.g., lorazepam, clonazepam. Lithium can also be administered. Thus, in some embodiments, the methods can include the administration of one or more antidepressant and/or anti-anxiety medications to a person identified as at risk of developing SZ, SPD, or SD.

The methods can also include psychosocial and rehabilitation interventions, e.g., interventions that are generally accepted as therapeutically beneficial, e.g., cognitive-behavioral therapy for treatment-resistant positive psychotic symptoms; supportive, problem-solving, educationally oriented psychotherapy; family therapy and education programs aimed at helping patients and their families understand the patient's illness, reduce stress, and enhance coping capabilities; social and living skills training; supported employment programs; and/or the provision of supervised residential living arrangements.

Currently accepted treatments for SZ are described in greater detail in the *Practice Guideline for the Treatment of Patients With Schizophrenia American Psychiatric Association*, Second Edition, American Psychiatric Association, 2004, which is incorporated herein by reference in its entirety.

Methods of Determining Treatment Regimens and Methods of Treating SZ, SPD or SD

As described herein, the presence of haplotypes described herein has been correlated with an increased risk of developing or having SZ, SPD, or SD. Thus, the new methods can also include selecting a treatment regimen for a subject determined to be at risk for developing SZ, SPD or SD, based upon the absence or presence of a haplotype associated with SZ as described herein. The determination of a treatment regimen can also be based upon the absence or presence of other risk factors associated with SZ, e.g., as described herein. Therefore, the methods of the invention can include selecting a treatment regimen for a subject having one or more risk factors for SZ, and having a haplotype described herein. The methods can also include administering a treatment regimen to a subject having, or at risk for developing, SZ to thereby treat, prevent or delay further progression of the disease. A treatment regimen can include the administration of antipsychotic medications to a subject identified as at risk of developing SZ before the onset of any psychotic episodes.

As used herein, the term "treat" or "treatment" is defined as the application or administration of a treatment regimen, e.g., a therapeutic agent or modality, to a subject, e.g., a patient. The subject can be a patient having SZ, a symptom of SZ or at risk of developing (i.e., a predisposition toward) SZ. The treatment can be to cure, heal, alleviate, relieve, alter, remedy, ameliorate, palliate, improve or affect SZ, the symptoms of SZ or the predisposition toward SZ.

The methods of the invention, e.g., methods of determining a treatment regimen and methods of treatment or prevention of SZ, can further include the step of monitoring the subject, e.g., for a change (e.g., an increase or decrease) in one or more of the diagnostic criteria for SZ listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for SZ can be evaluated by administering the same treatment or combinations or treatments to a subject having SZ, SPD or SD and a haplotype as described herein and to a subject that has SZ but does not have a haplotype as described herein. The effects of the treatment or combination of treatments on each of these subjects can be used to determine if a treatment or combination of treatments is particularly effective on a sub-group of subjects having SZ, SPD or SD. In other embodiments, various treatments or combinations of treatments can be evaluated by administering two different treatments or combinations of treatments to at least two different subjects having SZ, SPD or SD and a haplotype as described herein. Such methods can be used to determine if a particular treatment or combination of treatments is more effective than others in treating this subset of SZ, SPD and/or SD patients.

Various treatment regimens are known for treating SZ, e.g., as described herein.

Pharmacogenomics

With regards to both prophylactic and therapeutic methods of treatment of SZ, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market. See, for example, Eichelbaum et al., Clin. Exp. Pharmacol. Physiol. 23:983-985 (1996) and Linder et al., Clin. Chem. 43:254-266 (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing SZ.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, a physician or clinician may determine (or have determined, e.g., by a laboratory) the haplotype of a subject as described herein, and optionally one or more other markers associated with SZ, SPD, or SD, of one or a group of subjects who may be participating in a clinical trial, wherein the subjects have SZ, SPD, or SD, and the clinical trial is designed to test the efficacy of a pharmaceutical composition, e.g., an antipsychotic or combination of antipsychotic agents, and wherein the physician or clinician attempts to correlate the genotypes of the subjects with their response to the pharmaceutical composition.

As another example, information regarding a haplotype associated with an increased risk of SZ, SPD or SD, as described herein, can be used to stratify or select a subject population for a clinical trial. The information can, in some embodiments, be used to stratify individuals that may exhibit a toxic response to a treatment from those that will not. In other cases, the information can be used to separate those that will be non-responders from those who will be responders. The haplotypes described herein can be used in pharmacogenomics-based design and manage the conduct of a clinical trial, e.g., as described in U.S. Pat. Pub. No. 2003/0108938.

As another example, information regarding a haplotype associated with an increased risk of SZ, SPD or SD, as described herein, can be used to stratify or select human cells or cell lines for drug testing purposes. Human cells are useful for studying the effect of a polymorphism on physiological function, and for identifying and/or evaluating potential therapeutic agents for the treatment of SZ, SPD, or SD, e.g., anti-psychotics. Thus the methods can include performing the present methods on genetic material from a cell line. The information can, in some embodiments, be used to separate cells that respond particular drugs from those that do not respond, e.g. which cells show altered second messenger signaling.

Theranostics

Also included herein are compositions and methods for the identification and treatment of subjects who have an increased risk of SZ, SPD or SD, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to SZ, SPD or SD, the methods and compositions described herein also provide a means of optimizing the treatment of a subject having such a disorder. Provided herein is a theranostic approach to treating and preventing SZ, SPD or SD, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a haplotype as described herein and any measurable or quantifiable parameter relating to the outcome of the treatment, e.g., efficacy (the results of which may be binary (i.e., yes and no) as well as along a continuum), side-effect profile (e.g., weight gain, metabolic dysfunction, lipid dysfunction, movement disorders, or extrapyramidal symptoms), treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a selected haplotype can influence treatment such that the treatment is recommended or selected for a subject having the selected haplotype.

Kits

Also within the scope of the invention are kits comprising a probe that hybridizes with a region of human chromosome as described herein and can be used to detect a polymorphism described herein. The kit can include one or more other elements including: instructions for use; and other reagents, e.g., a label, or an agent useful for attaching a label to the probe. Instructions for use can include instructions for diagnostic applications of the probe for assessing risk of SZ in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to the same chromosome, e.g., chromosome 4 or 22, or another chromosome or portion thereof that can have an abnormality associated with risk for SZ. For example, the additional probe or probes can be: a probe that hybridizes to human chromosome 22q11-12 or a portion thereof, (e.g., a probe that detects a sequence associated with SZ in this region of chromosome 22), or probes that hybridize to all or a portion of 22q12.3 (e.g., near D22S283), 22q11.2, 22q11.2, 22q11-q13, 1q42.1, 1q42.1, 18p, 15q15, 14q32.3, 13q34, 13q32, 12q24, 11q14-q21, 1q21-q22, 10p15-p13 (e.g., near D10S189), 10q22.3, 8p21, 6q13-q26, 6p22.3, 6p23, 5q11.2-q13.3, and/or 3p25. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to SZ, SPD or SD as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular haplotype and the information regarding the subject, e.g., to detect correlations between a haplotype and a particular endophenotype, or treatment response.

Engineered Cells

Also provided herein are engineered cells that harbor one or more polymorphism described herein, e.g., one or more polymorphisms that constitute a haplotype associated with SZ, SPD, or SD. Such cells are useful for studying the effect of a polymorphism on physiological function, and for identifying and/or evaluating potential therapeutic agents for the treatment of SZ, SPD, or SD, e.g., anti-psychotics.

As one example, included herein are cells in which one of the various alleles of the genes described herein has be recreated that is associated with an increased risk of SZ, SD, or SPD. Methods are known in the art for generating cells, e.g., by homologous recombination between the endogenous gene and an exogenous DNA molecule introduced into a cell, e.g., a cell of an animal. In some embodiments, the cells can be used to generate transgenic animals using methods known in the art.

The cells are preferably mammalian cells, e.g., neuronal type cells, in which an endogenous gene has been altered to include a polymorphism as described herein. Techniques such as targeted homologous recombinations, can be used to insert the heterologous DNA as described in, e.g., Chappel, U.S. Pat. No. 5,272,071; WO 91/06667, published in May 16, 1991.

The invention is further described in the following examples, which do not limit the scope of the invention described in the claims.

EXAMPLES

Example 1

Whole Autosomal Screen for Quantitative Trait Loci (QTLs) Influencing Adult Schizotypy 640 adult offspring and their parents in 165 families who have participated in the longitudinal Louisville Twin Study of behavioral development were recruited and their informed consent to participate in this project was obtained. The offspring form 1,150 twin and sibling pairs. The sample includes 21 dizygotic (DZ, i.e., fraternal) male, and 21 opposite-sexed twin pairs; 58 monozygotic (MZ, i.e., identical) female and 21 MZ male pairs; and 316 female, 215 male and 467 opposite sibling pairs. MZ twin pairs do not aid in linkage detection but permit monitoring of estimates of shared environmental and residual additive genetic variance.

The MMPI-2 is the slightly revised form of a well-verified personality questionnaire that has been widely used for decades in research and clinical settings. The basic clinical scales were created to differentiate empirically between diagnosed persons and controls (Hathaway and McKinley (1989), Manual for the MINNESOTA MULTIPHASIC PERSONALITY INVENTORY-2™ (MMPI-2™) Minneapolis, University of Minnesota Press). In the present study, MMPI-2 questionnaires were scored and scaled by computer, using procedures and tables provided by Hathaway and McKinley (Hathaway and McKinley (1989), supra), including the K-correction for defensive responding. The whole autosomal screen was performed on standardized, untransformed MMPI-2 scaled scores. Subsequently, the scores were transformed using the natural log to reduce the influence of outlying scores on the results. Regression procedures are generally quite robust with respect to non-normality, but the influence of outliers must be evaluated. For all scales the log-transform was sufficient to meet the criteria of no probable outliers in the standard box plot procedure as implemented in Minitab statistical software (Minitab, Inc.).

Genotypes were determined at 227 polymorphic markers (mean heterozygosity 0.81) with an average spacing of 16.2 cM. We used standardized procedures for fluorescently-labeled primers (Applied Biosystems, approximately 85% of genotypes) or $^{32}$P-labeled primers (Scored on a Molecular Dynamics phosphoimager, 15% of genotypes) as described previously (Brennan et al., (2000) Genomics 63: 430-432). Genetic maps were constructed using MultiMap (Matise et al., (1994) Nat. Genet. 6: 384-390). The genetic map derived for chromosome 4 markers is shown in Table 1 and the map for chromosome 22 markers, was as previously described (Brennan et al., (2000), supra).

TABLE 1

Microsatellite Markers for Chromosome 4

| Marker | MB[b] | Kosambi cM | | |
| --- | --- | --- | --- | --- |
| | | Female | Male | Sex Averaged |
| D4s126 | 30.22495 | 0 | 0 | 0 |
| D4s1599[a] | NA | 27.4 | 14.1 | 20.1 |
| D4s391 | 27.221546 | 57.2 | 33.5 | 43.6 |
| D4s174 | 40.528682 | 76.3 | 43.8 | 57.9 |
| D4s1645 | 61.665571 | 103.2 | 47.6 | 71.1 |
| D4s423 | 92.691891 | 158 | 67.2 | 102 |
| D4s406 | 111.93789 | 177 | 80.8 | 118.5 |
| D4s402 | 120.36763 | 187.7 | 86.1 | 126.4 |
| D4sIL-2 | 123.53890 | 192.5 | 89.3 | 130.5 |

TABLE 1-continued

Microsatellite Markers for Chromosome 4

| Marker | MB[b] | Kosambi cM | | |
|---|---|---|---|---|
| | | Female | Male | Sex Averaged |
| D4s175 | 139.58611 | 212.8 | 94.2 | 142.2 |
| FGA (UniSTS: 156198) | 155.72822 | 232.9 | 105.5 | 157.2 |
| D4s1636 | 166.73249 | 251.7 | 112.6 | 169.2 |
| D4s1554 | 184.92558 | 287.6 | 131.4 | 194.7 |
| D4s2930 | 190.33384 | 300.9 | 152.4 | 211.3 |

Footnotes Table 1:
[a]Not placed on physical map.
[b]Genome Build 36.2

Proportions identical by descent (IBD) were estimated for sibling and DZ twin pairs at 3,343 1-cM points across the 22 autosomes using MAPMAKER/Sib (Kruglyak and Lander, (1995) Am. J. Hum. Genet. 57: 439-454). Linkage analyses were performed using a multiple regression procedure (Fulker et al., (1995) Am. J. Hum. Genet. 56: 1224-1233):

$$P1_i = b_0 + b_1 P2_i + b_2 \pi_{ij} + b_3 P2_i \pi_{ij} + b_4 \pi_{iR} + b_5 P2_i \pi_{iR}$$

Here $P1_i$ and $P2_i$ are the personality scores of the ith sibling or twin pair; $\pi_{ij}$ is the estimated proportion of chromosomal material IBD for the ith pair at the jth 1-cM point on a chromosome; the $\pi_{iR}$ is the overall coefficient of relationship of the ith pair, 0.5 for DZ twins and sibling pairs and 1.0 for MZ pairs. For each chromosomal point, the t-value for $b_3$ was evaluated for evidence of linkage. One-tailed probabilities were calculated from the normal distribution, which applies in large samples.

PCR Amplification and Genotyping

Microsatellite markers were genotyped following standard procedures with 10 ng genomic DNA in 10 μl reaction volumes, using PCR reagents obtained from Applied Biosystems (ABI, Foster City, Calif.), with standard reaction conditions as described previously (Brennan et al., (2000) Genomics 63, 430-432; Brennan and Condra, (2005) Am. J. Med. Genet. B Neuropsychiatr. Genet. 139, 69-72). Fragments were analyzed using an ABI PRISM 377 DNA sequencer, with GeneScan and Genotyper software packages followed by manual confirmation.

Genetic Analysis

Mendelian inheritance for all markers was confirmed using the GENEHUNTER genetic analysis software (Version 2.0; Kruglyak et al., (1996) Am. J. Hum. Genet. 58, 1347-1363). Following initial analysis, putatively recombinant chromosomes were identified to detect possible genotyping errors, and genotyping was repeated to confirm recombination events. As a reference genetic map, a map previously based upon approximately 1000 informative meioses for chromosome 22q (Brennan et al., (2000), supra) was used. Input allele frequencies for microsatellite markers were the empirical frequencies determined for approximately 550 unrelated individuals from the Louisville metropolitan area (Brennan et al., (2000), supra).

Figure 2:
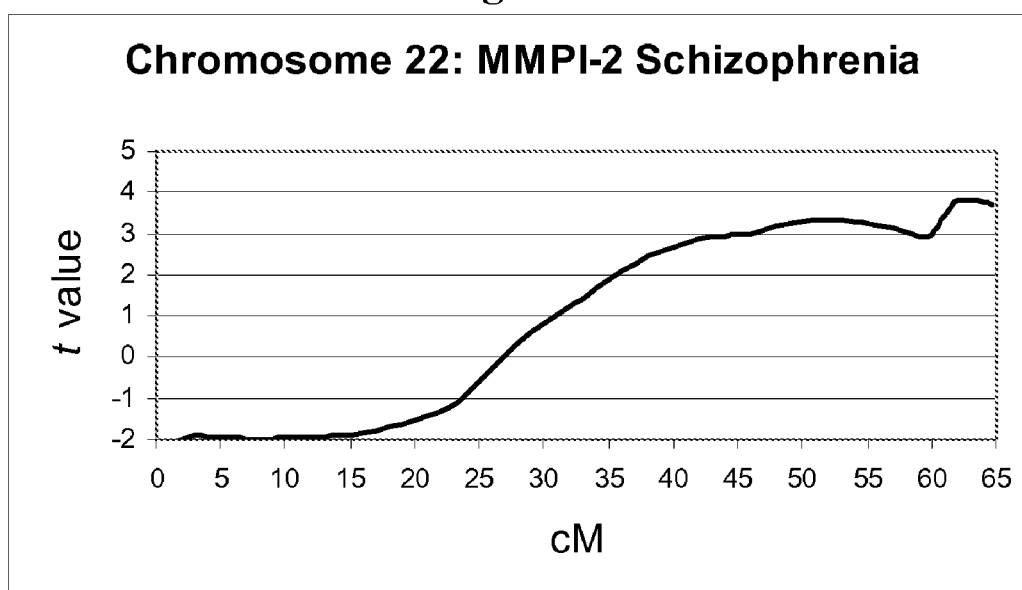
FIG. 2 is a line graph showing the results of QTL linkage analysis for MMPI-2 schizophrenia scale for chromosome 22. Abscissa shows linkage t-values and ordinate shows position along the chromosome in cM. Both the peak at 52 cM and that at 63 cM exceed the t-value of 3.19 ($P=7\times10^{-4}$), proposed criterion for "suggestive" linkage for complex genetic traits (Kruglyak and Lander, (1995) Am. J. Hum. Genet. 57: 439-454).

Analysis of the linkage t-value across the 22 autosomes for the MMPI-2 schizophrenia scale revealed two major peaks. There was a significant linkages on 4p15.1 spanning D4S391 (t=4.34, P=7×10$^{-6}$), at 41-45 cM from p-ter (FIG. 1). Chromosome 22q had two peaks, a major peak on 22q13.33 at 63 cM, about midway between markers D22S526 and D22S1744 (t=3.83, P=6×10$^{-5}$), located at 61.8 and 64.6 cM from the p-ter respectively, and a somewhat lower peak located at 52 cM (t=3.34, P=4.2×10$^{-4}$) (FIG. 2).

The MMPI-2 validity K-scale was tested in both the 4p15 and 22q13 regions. The K-scale is used to correct five of the basic clinical scales for defensive responding, including the schizophrenia and psychasthenia scales (Hathaway and McKinley (1989), supra). There was no indication of linkage for the K-scale in either region, indicating that the K-correction was not a source for the linkages.

Example 2

Chromosome 4p Detailed Studies by QTL Linkage Analysis for MMP-Scales

The findings on chromosome 4 were explored with eight other MMPI-2 basic clinical scales: the results are shown in Table 2.

TABLE 2

MMPI-2 QTL linkages on Chromosome 4p for Basic Clinical Scales

| Linkage Peak cM | MMPI-2 Scale | t value | P value |
|---|---|---|---|
| 41-45 | schizophrenia (schizotypy) | 4.34 | 0.000007 |
| 40-41 | psychasthenia (obsessive-compulsive) | 3.83 | 0.000063 |
| 43 | psychopathic deviance | 3.17 | 0.00076 |
| 39 | Hysteria | 2.84 | 0.0022 |
| 47 | hypochondriasis | 2.59 | 0.0048 |
| 44 | depression | 2.26 | 0.012 |
| 40 | mania | 2.22 | 0.013 |

The psychasthenia scale (Hathaway and McKinley (1989), Manual for the MINNESOTA MULTIPHASIC PERSONALITY INVENTORY-2™ (MMPI-2™) Minneapolis, University of Minnesota Press) a measure of obsessive-compulsiveness, showed linkage (t=3.83, P=6×10$^{-5}$) in this region, and five other basic clinical scales—hysteria, psychopathic deviance, hypochondriasis, depression and mania (Hathaway and McKinley (1989), supra)—were elevated in this region as well. A total of seven of the basic clinical scales of the MMPI-2, thus, formed a striking, nearly uniform pattern of elevation near D4S391. Although the MMPI-2 scales are correlated, this does not account for the pattern found on 4p because the scales show scattered patterns seen for these linkages elsewhere in the QTL scan.

The 4p15 region was also probed with additional scales and subscales: the six Harris-Lingoes schizophrenia subscales (Hathaway and McKinley (1989), supra; Butcher et al., (1989) Development and use of the MMPI-2 content scales. University of Minnesota Press, Minneapolis; the content scales (Hathaway and McKinley (1989), supra) for obsessiveness, fears and bizarre mentation; and the ten Weiner-Harmonl subtle vs. obvious subscales. Six of the subscales showed linkage in this region, and interestingly, their peaks only partially coincided with those for schizophrenia and psychasthenia (Table 3).

TABLE 3

MMPI-2 QTL linkages on Chromosome 4p for Subscales

| Linkage Peak cM | MMPI-2 Scale | t value | P value |
|---|---|---|---|
| 43-44 | paranoia obvious | 3.46 | 0.00027 |
| 39 | hysteria obvious | 3.99 | 0.000033 |
| 39-41 | anxiety | 3.20 | 0.00068 |
| 34 | obsessiveness | 4.72 | 0.0000012 |

TABLE 3-continued

MMPI-2 QTL linkages on Chromosome 4p for Subscales

| Linkage Peak cM | MMPI-2 Scale | t value | P value |
|---|---|---|---|
| 31 | Sc6 subscale (bizarre sensory) | 4.30 | 0.0000085 |
| 29 | Sc5 subscale (lack of ego mastery, defective inhibition) | 3.39 | 0.00034 |

The paranoia obvious subscale showed linkage (=3.46, P=2.7×10$^{-4}$) at 43-44 cM, the peak area for the schizophrenia scale. The hysteria obvious subscale showed linkage (=3.99, P=3.3×10$^{-5}$) at 39 cM, near the peak for the psychasthenia scale, as did the anxiety scale (t=3.2, P=7×10$^{-4}$) at 39-41 cM. The obsessiveness content scale revealed a highly significant linkage (=4.72, P=1.2×10$^{-6}$) at 34 cM, which is five cM distal to the peak for psychasthenia. The schizophrenia Sc6 subscale, a measure of bizarre sensory experiences, revealed a significant linkage (=4.30, P=8.6×10$^{-6}$) at 31 cM, and the schizophrenia Sc5 subscale, a measure of lack of ego mastery and defective inhibition, gave a peak at 29 cM (=3.39, P=3.4× 10$^{-4}$).

These results suggest that there are at least two separable QTLs influencing aspects of schizotypy (e.g., schizophrenia susceptibility) and related personality and psychopathology in the 4p15 region. Log transformation had little effect, slightly reducing the peak linkage=values from 4.34 to 4.10 for schizophrenia and from 3.83 to 3.44 for psychasthenia and without changing the locations of the maximums (not shown). This indicates that the influence of extreme scores on these results is small.

Example 3

Chromosome 4p Gene Confirmation by TDT in Clinical Samples

Samples from thirty-nine families, comprising 212 individuals, each having multiple affected siblings were obtained from NIMH. Self-description of heritage was as follows: African-American, 14 families; European/Mediterranean, 25 families. DSM-IIIR or DSM-IV criteria were compiled for all subjects by researchers at Columbia University, Harvard University and Washington University. Detailed information on ascertainment, diagnosis and informed consent has been previously provided by these groups (Cloninger et al., (1998) Am. J. Med. Genet. 81, 275-281; Faraone et al., (1998) Am. J. Med. Genet. 81, 290-295; Kaufmann et al., (1998) Am. J. Med. Genet. 81, 282-289).

Using the DSM-IIIR/IV criteria for SZ, the sample contained 51 affected sibling pairs, and using a broadest disease definition that included schizotypal personality disorder and schizoaffective disorder, the sample contained 91 affected sibling pairs.

SNPs were genotyped by ABI ASSAYS-ON-DEMAND™ genotyping kits using the conditions suggested by the supplier (5 μl reactions in 384-well plates, containing 4.5 ng genomic DNA). PCR products were analyzed using the ABI Prism 7900HT Sequence Detection System. In cases where a reaction failed (<3% of total), or the results were not consistent with Mendelian inheritance (<0.5% of total), a second reaction was carried out to resolve discrepancies.

Transmission disequilibrium (TDT) analysis was performed to test for the possibility of allelic association in the presence linkage (Laird and Lange, (2006) Nat. Rev. Genet. 7, 385-394). TDT analysis was performed using TRANSMIT (Version 2.5.2), which uses a robust variance estimate that allows for multiple affected members in each family, in effect, treating families, rather than siblings, as independent entities (Clayton, (1999) Am. J. Hum. Genet. 65, 1170-1177; Martin et al., (2003) Am. J. Hum. Genet. 73, 1016-1026). Alleles were aggregated so as to prevent elevation of $X^2$ values that can arise due to expectations for rare haplotypes. The resulting global $X^2$ analyses estimate the significance of the transmission distribution for all alleles combined, with rare haplotypes being treated as a single group. Similarly, $X^2$ values for transmission of individual alleles, with one degree of freedom, were determined by TRANSMIT. We used two approaches to arrive at conservative estimates of Type I error probabilities for TDT analysis. First, Bonferroni corrections for multiple comparisons were applied. Second, 10,000 bootstrap replicates in TRANSMIT were used to determine empirical probabilities. The latter approach is particularly conservative, as it randomly samples a single affected individual for each family.

The chromosome 4p region was broken into two segments to look for novel candidate genes: (1) 29-34 cM and (2) 39-43 cM. First, public databases were searched for genes in the region near 31-34 cM (corresponding to 19-22 mB on the reference assembly), and candidate genes were identified. TDT analysis was performed on these genes.

In the first segment (29-34 cM), one of the candidate genes, Kv channel interacting protein 4 (KCNIP4), was positive (see Table 4).

TABLE 4

TDT Analysis of KCNIP4 SNPs and Haplotypes

| | P values | | |
|---|---|---|---|
| SNPs/Haps rs6447982 - rs10016449 | SZ | SZ + SPD | SZ + SPD + SD |
| Global (3 df) | 0.068 | 0.18 | 0.19 |
| A - T haplotype over-transmitted (1 df) | 0.03 | 0.18 | 0.25 |
| A - C haplotype under-transmitted (1 df) | 0.16 | 0.15 | 0.22 | rs#: is the universal SNP identifier used by NCBI (e.g. rs12641357 will return an unique SNP in the human genome sequence). The P values shown are for TDT analysis. Values less than 0.05 are nominally significant and those less than 0.01 are highly significant.
sz = disease definition is schizophrenia
sz + sd = broader disease definition including schizotypal personality disorder
sz + sd + spd = broadest disease definition including schizoaffective disorder

TABLE 5

Bootstrap Replication Analysis of KCNIP4 SNPs and Haplotypes

| SNPs/Haps rs6447982 - rs10016449 | SZ | SZ + SPD | SZ + SPD + SD |
|---|---|---|---|
| Global (3 df) | 0.023 | 0.110 | 0.16 |
| A - T haplotype over-transmitted (1 df) | 0.016 | 0.130 | 0.24 |
| A - C haplotype under-transmitted (1 df) | 0.05 | 0.081 | 0.16 |

Table 5 shows the results of bootstrap replication analyses (10,000 computer simulations; for selected SNPs and haplotypes only). This is a more conservative way of estimating P values. Low P values by this procedure are more likely to be real. The "maximum" values indicate that most significant values obtained for any particular haplotype (which could be "protective" or "susceptible"). The "global" values indicate that, as a group, the haplotypes are skewed in their transmission to affected offspring. For single SNPs the maximum and global scores theoretically should be equal. For haplotypes involving two or more SNPs, global values are often more significant, because they reflect the combined contributions from two or more haplotypes.

The marker D4s391 is at 43.5 cM on the map described above (placed also at about 43 to 44 cM on reference maps and corresponding to 27.2 mB on the reference assembly). The region from 39-43cM corresponds to 24 to 27 mB on the reference assembly.

In the second segment (39-43 cM), phosphatidylinositol 4-kinase type 2 beta (PI4K2B), at 24.8-24.9 mBase, was positive. The results are shown in Tables 6-7.

TABLE 6

TDT Analysis of PI4K2B SNPs and Haplotypes

| | P values | | |
|---|---|---|---|
| SNPs/Haps rs313548 | SZ | SZ + SPD | SZ + SPD + SD |
| Global (1 df) | 0.036 | 0.018 | 0.019 |
| C allele over-transmitted (1 df) | 0.036 | 0.018 | 0.019 | rs#: is the universal SNP identifier used by NCBI. The P values shown are for TDT analysis. Values less than 0.05 are nominally significant and those less than 0.01 are highly significant.
sz = disease definition is schizophrenia
sz + sd = broader disease definition including schizotypal personality disorder
sz + sd + spd = broadest disease definition including schizoaffective disorder

TABLE 7

Bootstrap Replication Analysis of PI4K2B SNPs and Haplotypes

| SNPs/Haps rs313548 | SZ | SZ + SPD | SZ + SPD + SD |
|---|---|---|---|
| Global (1 df) | 0.031 | 0.02 | 0.042 |
| C allele over-transmitted (1 df) | 0.031 | 0.02 | 0.042 |

Thus, SNPs/Haps in the genes KCNIP and PI4K2B on chromosome 4p are associated with an increased risk of developing SZ, SPD, or SD.

Example 4

Chromosome 22q Detailed QTL Linkage Analysis for MMPI-Scales

The area on chromosome 22q13 was also explored by testing other basic clinical scales and subscales in this region. Only one other basic clinical scale—hypochondriasis (Hathaway and McKinley (1989), supra)—showed elevation in the 22q-ter region with a maximum t=3.05 (P=1.2×10$^{-3}$) at our most distal marker, D11S1743, at 64.7 cM and physically about 10 kb proximal to the coding regions of the ARSA gene (Brennan et al., (2000), supra). The results are shown in Table 8.

TABLE 8

MMPI-2 QTL linkages on Chromosome 22q for Clinical Scales

| Linkage Peak cM | MMPI-2 Scale | t value | P value |
|---|---|---|---|
| 63 | Schizophrenia (schizotypy) | 3.83 | 0.00006 |
| 52-53 | Schizophrenia (schizotypy) | 3.34 | 0.00042 |
| 64.7 | hypochondriasis | 3.05 | 0.0012 |
| 52-54 | hypochondriasis | 2.81 | 0.0024 |

As before, log-transformation had only a small effect. It did not change the location of the peak at 63 cM, but the t value decrease slightly (t=3.63 vs. 3.83). Similarly, for the secondary peak at 52 cM, the position did not move, but the t value changed slightly, this time being somewhat higher for the log-transformed scale (t=3.55 vs. 3.34). As was seen for chromosome 4, the results for the log-transformed scores indicate that the contribution/influence of extreme scores on these linkage results is small.

Example 5

Chromosome 22q Gene Confirmation by TDT in Clinical Samples

TDT analysis was performed on the identified region of 22q as described above in Example 3. This region was broken into two segments: (1) 52-53 cM and (2) 63-65 cM, to look for novel candidate genes.

First, public databases were searched for genes in these regions, and candidate genes were identified for the 52-53 cM region. Of those candidates, CERK (45.46-45.51 mBase, known as "FJ23239", a diacylglycerol kinase gene of then unknown function), was positive (see Tables 9-10).

TABLE 9

TDT Analysis of CERK SNPs and Haplotypes

| | P values | | |
|---|---|---|---|
| SNPs/Haps | SZ | SZ + SPD | SZ + SPD + SD |
| rs1548977 | | | |
| Global (1 df) | 0.045 | >0.05 | >0.05 |
| A allele over-transmitted (1 df) | 0.045 | >0.05 | >0.05 |
| rs135667 - rs1548977 | | | |
| Global (3 df) | 0.0016 | 0.017 | 0.011 |
| G - A haplotype over-transmitted (1 df) | 0.0085 | 0.055 | 0.029 |
| G - G haplotype under-transmitted (1 df) | 0.0036 | 0.09 | 0.021 |
| rs135678 - rs135693 | | | |
| Global (3 df) | 0.14 | 0.024 | 0.018 |
| T - C haplotype over-transmitted (1 df) | 0.069 | 0.024 | 0.013 | rs#: is the universal SNP identifier used by NCBI. The P values shown are for TDT analysis. Values less than 0.05 are nominally significant and those less than 0.01 are highly significant.
sz = disease definition is schizophrenia
sz + sd = broader disease definition including schizotypal personality disorder
sz + sd + spd = broadest disease definition including schizoaffective disorder

TABLE 10

Bootstrap Replication Analysis of CERK SNPs and Haplotypes

| | Bootstrap Replication | | |
|---|---|---|---|
| SNPs/Haps | SZ | SZ + SPD | SZ + SPD + SD |
| rs1548977 | | | |
| Global (1 df) | 0.042 | >0.05 | >0.05 |
| A allele over-transmitted (1 df) | 0.042 | >0.05 | >0.05 |
| rs135667 - rs1548977 | | | |
| Global (3 df) | 0.0098 | 0.053 | 0.064 |
| G - A haplotype over-transmitted (1 df) | 0.0038 | 0.039 | 0.016 |
| G - G haplotype under-transmitted (1 df) | 0.0055 | 0.053 | 0.018 |
| rs135678 - rs135693 | | | |
| Global (3 df) | 0.1 | 0.02 | 0.02 |
| T - C haplotype over-transmitted (1 df) | 0.11 | 0.041 | 0.024 |

Table 10 shows the results of bootstrap replication analyses for the positive SNPs and haplotypes identified in CERK, performed as described above in Example 3.

Public database searching for candidate genes in the second region, 63-65 cM, identified SH3 and multiple ankyrin repeat domains 3 (SHANK3, at 49.46-49.52 mBase). The results of TDT analysis of SHANK3 SNPs and Haplotypes are shown in Tables 11-12.

TABLE 11

TDT Analysis of SHANK3 SNPs and Haplotypes

| SNPs | P values | | |
|---|---|---|---|
| | SZ | SZ + SPD | SZ + SPD + SD |
| rs9616816 | | | |
| Global (1 df) | 0.0095 | 0.0051 | 0.0011 |
| A allele over-transmitted (1 df) | 0.0095 | 0.0051 | 0.0011 |
| rs713692 - rs9616816 | | | |
| Global (3 df) | 0.10 | 0.06 | 0.02 |
| C - A haplotype over-transmitted (1 df) | 0.06 | 0.03 | 0.015 |
| C - G haplotype under-transmitted (1 df) | 0.12 | 0.19 | 0.09 |
| rs9616915 - rs9616816 | | | |
| Global (3 df) | 0.028 | 0.0055 | 0.0017 |
| T - A haplotype over-transmitted (1 df) | 0.087 | 0.058 | 0.05 |
| C - G haplotype under-transmitted (1 df) | 0.013 | 0.0014 | 0.001 |
| rs9616816-rs739365 | | | |
| Global (3 df) | 0.066 | 0.03 | 0.084 |
| A - C haplotype over-transmitted (1 df) | 0.18 | 0.069 | 0.024 |
| G - C haplotype under-transmitted (1 df) | 0.021 | 0.01 | 0.0072 |
| rs9616816-rs6010063 | | | |
| Global (3 df) | 0.0089 | 0.017 | 0.0033 |
| A - A haplotype over-transmitted (1 df) | 0.006 | 0.016 | 0.0033 |
| G - G haplotype under-transmitted (1 df) | 0.021 | 0.055 | 0.03 |
| rs713692 - rs 756638 | | | |
| Global (3 df) | 0.37 | 0.034 | 0.014 |
| C - A haplotype under-transmitted (1 df) | 0.14 | 0.0063 | 0.0015 | rs#: is the universal SNP identifier used by NCBI. The P values shown are for TDT analysis. Values less than 0.05 are nominally significant and those less than 0.01 are highly significant.
sz = disease definition is schizophrenia
sz + sd = broader disease definition including schizotypal personality disorder
sz + sd + spd = broadest disease definition including schizoaffective disorder

TABLE 12

Bootstrap Replication Analysis of SHANK3 SNPs and Haplotypes

| SNPs | Bootstrap Replication | | |
|---|---|---|---|
| | SZ | SZ + SPD | SZ + SPD + SD |
| rs9616816 | | | |
| Global (1 df) | 0.042 | 0.0023 | 0.0003 |
| A allele over-transmitted (1 df) | 0.042 | 0.0023 | 0.0003 |
| rs713692 - rs9616816 | | | |
| Global (3 df) | 0.08 | 0.12 | 0.051 |
| C - A haplotype over-transmitted (1 df) | 0.03 | 0.068 | 0.035 |
| C - G haplotype under-transmitted (1 df) | 0.13 | 0.23 | 0.120 |
| rs9616915 - rs9616816 | | | |
| Global (3 df) | 0.040 | 0.011 | 0.0037 |
| T - A haplotype over-transmitted (1 df) | 0.021 | 0.032 | 0.027 |
| C - G haplotype under-transmitted (1 df) | 0.0095 | 0.0004 | 0.0004 |
| rs9616816-rs739365 | | | |
| Global (3 df) | 0.0034 | 0.011 | 0.0025 |
| A - C haplotype over-transmitted (1 df) | 0.068 | 0.0042 | 0.0001 |
| G - C haplotype under-transmitted (1 df) | 0.0004 | 0.0002 | 0.00003 |
| rs9616816-rs6010063 | | | |
| Global (3 df) | 0.0001 | 0.0031 | 0.0014 |
| A - A haplotype over-transmitted (1 df) | <0.0001 | 0.0033 | 0.0002 |
| G - G haplotype under-transmitted (1 df) | 0.0032 | 0.031 | 0.0037 |
| rs713692 - rs 756638 | | | |
| Global (3 df) | ND | ND | ND |
| C - A haplotype under-transmitted (1 df) | ND | ND | ND |

Table 12 shows the results of bootstrap replication analyses for the positive SNPs and haplotypes identified in SHANK3, performed as described above in Example 3.

Example 6

Exemplary SNPs within 1 LDU of Reference SNPs

Public database searches were used to identify exemplary SNPs within 1 LDU of the reference SNPs described herein. (From NCBI B36 assembly, dbSNP b126)

KCNP4

SNPs within 1 LDU of marker rs6447982 in European populations include: rs10031524, rs9995697, rs3764964, rs3764965, rs3764966, rs3764967, rs12331966, rs10017693, rs7681691, rs7688592, rs2052775, rs1985322, rs10022322, rs7655154, rs6811030, rs2288308, rs12640448, rs2162413, rs2114474, rs6811505, rs6831295, rs6831516, rs6447975, rs6447976, rs6447978, rs12644782, rs10084802, rs2322688, rs7689421, rs3816874, rs990206, rs7694208, rs6817475; in African populations include: rs10031524, rs10024002, rs9995697, rs7666288, rs3764964, rs3764965, rs3764966, rs12331966, rs10017693, rs7681691, rs7688592, rs2052775, rs10022322, rs7655154, rs9291412, rs6811030, rs2288308, rs2114474, rs6811505, rs6831516, rs6447975, rs6447976, rs6447978, rs12644782, rs10084802, rs2322688, rs7689421, rs3816874, rs990206, rs7694208; in Chinese populations include: rs10024002, rs9995697, rs3764964, rs3764965, rs3764966, rs3764967, rs12331966, rs10017693, rs7681691, rs2052775, rs10022322, rs7655154, rs6811030, rs2288308, rs12640448, rs2162413, rs6811505, rs6831295, rs6831516, rs6447975, rs6447976, rs6447978, rs12644782, rs10084802, rs2322688, rs990206, rs10938804, rs12641748; and in Japanese populations include: rs2162413, rs6831295, rs6831516, rs6447975, rs6447978, rs10084802, rs12641748.

SNPs within 1 LDU of marker rs10016449 in European populations include: rs16869961, rs16869962, rs1491363, rs1491364, rs923672, rs13118003, rs1546065, rs12331024, rs13149493, rs6843196, rs9998730, rs1907497, rs13130253, rs16869987, rs16869989, rsl1940825, rs7695244, rs7695774, rs10002199; in African populations include: rs13129008, rs3857162, rs1491363, rs1546065, rs6843196, rs9998730, rs1907497, rs16869987, rsl1940825, rs7695244; in Chinese populations include: rs16869962, rs1491363, rs13118003, rs16869987, rs16869989, rs10002199; and in Japanese populations include: rs16869962, rs1491363, rs16869987, rs16869989, rs10002199.

PI4K2B

SNPs within 1 LDU of marker rs313548 in European populations include: rs10939041, rs1909475, rs12505283, rs7682177, rs10939043, rs10517063, rs313568, rs313577, rs11940059, rs313567, rs3106321, rs6834255, rs12649921; in African populations include: rs10939047, rs1909475; in Chinese populations include: rs10939041, rs1909475, rs10517063, rs313568, rs313577, rs313567, rs3106321, rs6834255, rs12649921; and in Japanese populations include: rs313567, rs3106321, rs6834255, rs12649921, rs10517063, rs313568.

CERK

SNPs within 1 LDU of marker rs15478977 in European populations include: rs1548978, rs5769125, rs1861739, rs5769126, rs710123, rs809652, rs17221476, rs801643, rs5769118, rs4823873, rs12628356, rs4642050, rs738726, rs2080581; in African populations include: rs5769118, rs4823873, rs12628356, rs4642050, rs2080581; in Chinese populations include: rs1548978, rs5769125, rs1861739, rs5769126, rs9626899, rs5769118, rs4823873, rs12628356, rs4642050, rs738726, rs2080581; and in Japanese populations include: rs1548978, rs5769125, rs1861739, rs5769126, rs809652, rs17221476, rs801646, rs9626899, rs5769118, rs4823873, rs12628356, rs4642050, rs738726, rs2080581.

SNPs within 1 LDU of marker rs135667 in European populations include: rs135677, rs801709, rs135678, rs78424, rs135686; in African populations include: rs135668, rs801712, rs135677, rs801709, rs135678, rs885792, rs2542026, rs801724, rs801720, rs2542014; in Chinese populations include: rs135668, rs135677, rs801709, rs135678, rs135680, rs135681, rs135686; and in Japanese populations include: rs801709, rs135678, rs135680, rs135681, rs135686.

SNPs within 1 LDU of marker rs135678 in European populations include: rs78424, rs135686, rs801719, rs135668, rs135677, rs801709; in African populations include: rs885792, rs2542026, rs801724, rs801720, rs2542014, rs135667, rs135668, rs801712, rs135677, rs801709; in Chinese populations include: rs135680, rs135681, rs135686, rs135698, rs135667, rs135668, rs135677, rs801709; and in Japanese populations include: rs135680, rs135681, rs135686, rs135667, rs135668, rs135677, rs801709.

SNPs within 1 LDU of marker rs135693 in European populations include: rs135694, rs135695, rs85598, rs135697, rs135698, rs135688; in African populations include: rs135694, rs135695, rs135697, rs5769101, rs2076710, rs2542038, rs2542037, rs6008944, rs737136, rs885792, rs2748341, rs2748343, rs2542026, rs801724, rs2748348, rs801720, rs801719, rs2542014, rs5769083, rs801715, rs135676, rs78424, rs135688; in Chinese populations include: rs2076710, rs2542038, rs2542037, rs6008944, rs737136, rs885792, rs2748341, rs2748343, rs2542026, rs801724, rs2748348, rs801720, rs801719, rs2542014, rs5769083, rs801715, rs135676, rs78424, rs135688; and in Japanese populations include: rs135694, rs135695, rs135697, rs5769101, rs2748343, rs2542026, rs801724, rs2748348, rs801720, rs801719, rs2542014, rs5769083, rs801715, rs135676, rs78424, rs135688.

SHANK3

SNPs within 1 LDU of marker rs739365 in European populations include: rs8135777, rs5770820.

SNPs within 1 LDU of marker rs9616816 in European populations include: rs2341009, rs1001469; in African populations include: rs9616915, rs7284093; in Chinese populations include: rs7284093, rs2341009, rs8135777; and in Japanese populations include: rs7284093, rs2341009, rs8135777.

SNPs within 1 LDU of marker rs713692 in European populations include rs10854884; in African populations include: rs962185; rs9616812; and in Japanese populations include: rs9616913, rs9616915, rs5770819, rs6009951, rs601006, rs4040041, rs10854884, rs8138460, rs9616906, rs9616812.

SNPs within 1 LDU of marker rs9616915 in European populations include: rs10854884, rs8138460, rs9616906, rs9616812, rs9628185, rs9616913; in African populations include: rs8138460, rs9616913; in Chinese populations include: rs8138460, rs9616906, rs9616812, rs9628185, rs9616913; and in Japanese populations include: rs10854884, rs8138460, rs9616906, rs9616812, rs9628185, rs9616913.

SNPs within 1 LDU of marker rs6010063 in European populations include: rs6010065; in Chinese populations include: rs6010065, rs81337951; and in Japanese populations include: rs6010065, rs81337951.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a human subject's risk of developing schizophrenia, the method comprising determining a ceramide kinase gene (CERK) haplotype of the subject, wherein the CERK haplotype comprises alleles of single nucleotide polymorphisms rs135667 and rs1548977, and the subject has an increased risk of developing schizophrenia when the haplotype comprises a "G" allele at said single nucleotide polymorphism rs135667 and an "A" allele at said single nucleotide polymorphism rs1548977, and the subject has a decreased risk of developing schizophrenia when the haplotype comprises a "G" allele at said single nucleotide polymorphism rs135667 and a "G" allele at said single nucleotide polymorphism rs1548977.

2. The method of claim 1, wherein said determining the CERK haplotype comprises:
obtaining a sample comprising DNA from the subject; and
determining the identities of the alleles of single nucleotide polymorphisms rs135667 and rs1548977.

3. The method of claim 2, wherein the sample is obtained from the subject by a health care provider.

4. The method of claim 2, wherein the sample is provided by the subject without the assistance of a health care provider.

5. The method of claim 1, further comprising determining the presence or absence of one or more additional markers associated with schizophrenia.

6. The method of claim 1, wherein the subject has one or more risk factors associated with schizophrenia.

7. The method of claim 6, wherein the one or more of the risk factors associated with schizophrenia include: the subject has a relative with schizophrenia; the subject has eye tracking dysfunction; the subject has deficits in working memory; or the subject has mixed-handedness.

8. The method of claim 6, wherein the risk factors associated with schizophrenia include: the subject has one or more relatives who have or had schizophrenia and said one or more relatives include grandparents, parents, uncles, aunts, siblings, or children of the subject.

9. The method of claim 1, wherein the subject is a child or a fetus or an embryo, and one of the relatives of the subject has schizophrenia.

10. A method of determining a human subject's risk of developing schizophrenia, the method comprising determining a ceramide kinase gene (CERK) haplotype of the subject, wherein the CERK haplotype comprises an allele of single nucleotide polymorphism rs1548977, and the subject has an increased risk of developing schizophrenia when the haplotype comprises an "A" allele at said single nucleotide polymorphism rs1548977.

11. The method of claim 10, wherein said determining the CERK haplotype comprises: obtaining a sample comprising DNA from the subject; and determining the identity of the allele of single nucleotide polymorphism rs1548977.

12. The method of claim 11, wherein the sample is obtained from the subject by a health care provider.

13. The method of claim 11, wherein the sample is provided by the subject without the assistance of a health care provider.

14. The method of claim 10, further comprising determining the presence or absence of one or more additional markers associated with schizophrenia.

15. The method of claim 10, wherein the subject has one or more risk factors associated with schizophrenia.

16. The method of claim 15, wherein the one or more of the risk factors associated with schizophrenia include: the subject has a relative with schizophrenia; the subject has eye tracking dysfunction; the subject has deficits in working memory; or the subject has mixed-handedness.

17. The method of claim 15, wherein the risk factors associated with schizophrenia include: the subject has one or more relatives who have or had schizophrenia and said one or more relatives include grandparents, parents, uncles, aunts, siblings, or children of the subject.

18. The method of claim 10, wherein the subject is a child or a fetus or an embryo, and one of the relatives of the subject has schizophrenia.

* * * * *